United States Patent [19]

Sholder

[11] Patent Number: 4,944,298
[45] Date of Patent: Jul. 31, 1990

[54] ATRIAL RATE BASED PROGRAMMABLE PACEMAKER WITH AUTOMATIC MODE SWITCHING MEANS

[75] Inventor: Jason A. Sholder, Northridge, Calif.

[73] Assignee: Siemens-Pacesetter, Inc., Sylmar, Calif.

[21] Appl. No.: 355,588

[22] Filed: May 23, 1989

[51] Int. Cl.$^5$ .............................................. A61N 1/00
[52] U.S. Cl. .............................................. 128/419 PG
[58] Field of Search ...................... 128/419 PG, 419 P

[56] References Cited

U.S. PATENT DOCUMENTS

| | | | |
|---|---|---|---|
| 4,305,396 | 12/1981 | Wittkampf et al. | 128/419 PG |
| 4,712,556 | 12/1987 | Baker, Jr. | 128/419 PG |
| 4,830,006 | 5/1989 | Haluska et al. | 128/419 PG |

Primary Examiner—Francis Jaworski
Assistant Examiner—George Manuel
Attorney, Agent, or Firm—Bryant R. Gold; Lisa P. Weinberg; Leslie S. Miller

[57] ABSTRACT

An atrial rate based programmable pacemaker including means for preventing the heart from being paced at an upper rate limit for prolonged periods of time is disclosed which paces the heart at a rate that follows or tracks the atrial rate up to the upper rate limit of the pacemaker, at which point the pacemaker stimulates the heart at the upper rate limit, but also continues to monitor the atrial rate. If the monitored atrial rate exceeds a second upper rate limit, a fast atrial arrhythmia or tachycardia condition is deemed to exist, and the pacemaker automatically switches from its existing mode of operation to an alternate mode of operation in an attempt to break or terminate the fast atrial condition. Alternate embodiments include using an external activity or physiological sensor to control the pacing rate in the new pacing mode, and the inclusion of means for periodically verifying that atrial sensing is occurring, and means for automatically adjusting the sensitivity of the atrial channel as required.

20 Claims, 5 Drawing Sheets

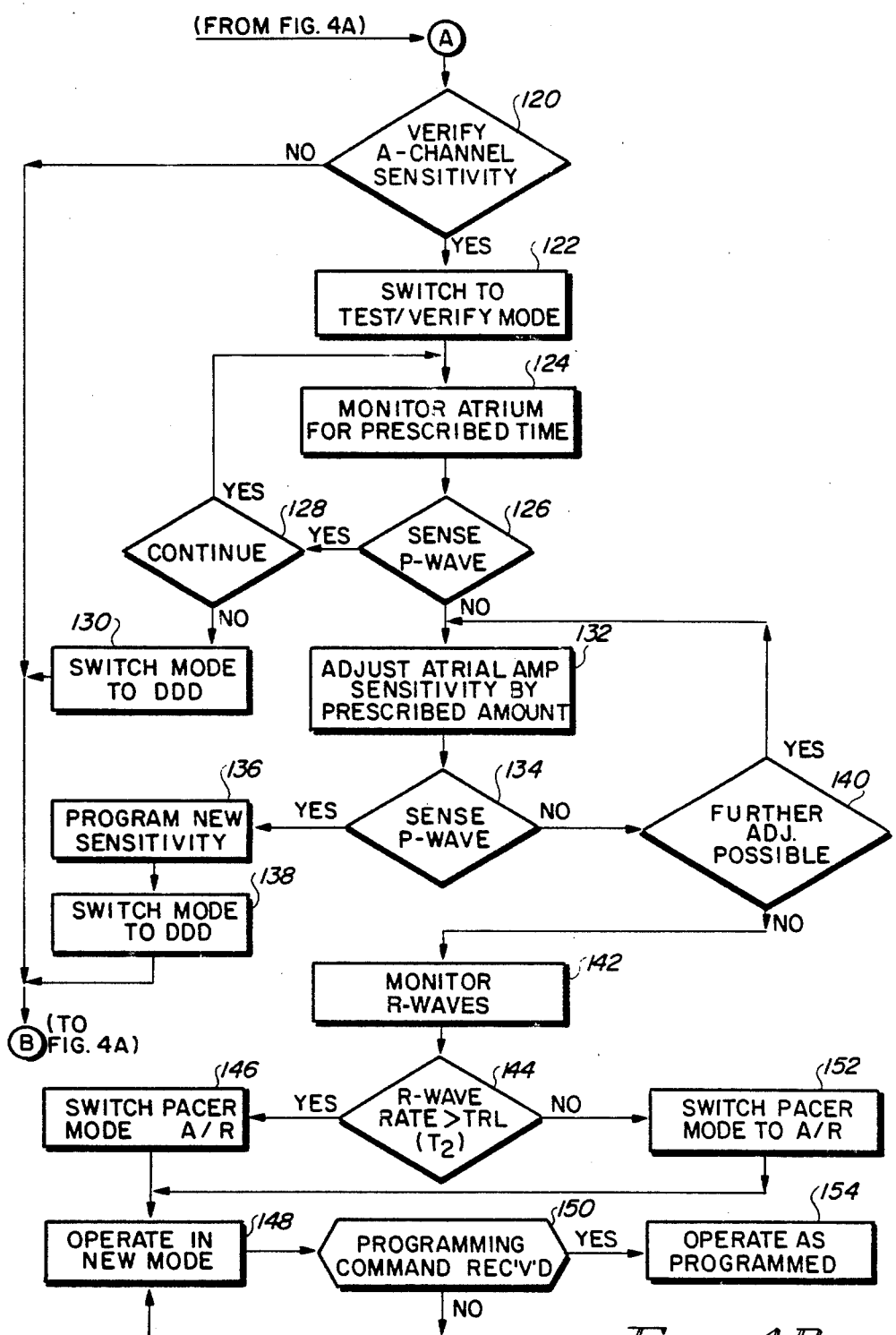

ATRIAL RATE BASED PROGRAMMABLE PACEMAKER WITH AUTOMATIC MODE SWITCHING MEANS

BACKGROUND OF THE INVENTION

Field of the Invention

The present invention relates generally to programmable implantable pacemakers, and more particularly to an implantable dual chamber pacemaker programmed to operate in an atrial rate based mode, wherein mode switching means are provided for automatically switching the mode of operation of the pacemaker from one mode to another in the event the sensed atrial rate exceeds a prescribed upper rate limit.

Modern programmable pacemakers are generally of two types: (1) single chamber pacemakers, and (2) dual chamber pacemakers In a single chamber pacemaker, the pacemaker provides stimulation pulses to, and/or senses cardiac activity within, a single chamber of the heart, e.g., either the right ventricle or the right atrium. In a dual chamber pacemaker, the pacemaker provides stimulation pulses to, and/or senses cardiac activity within, two chambers of the heart, e.g., both the right ventricle and the right atrium. Typically, only the right atrium and/or the right ventricle is coupled to the pacemaker because of the relative ease with which a pacing lead can be transvenously inserted into either of these chambers. However, the left atrium and left ventricle can also be paced just as effectively providing that suitable electrical contact is made therewith.

In general, both single and dual chamber pacemakers are classified by type according to a three letter code. In this code, the first letter identifies the chamber of the heart that is paced (i.e., that chamber where a stimulation pulse is delivered), with a "V" indicating the ventricle, an "A" indicating the atrium, and a "D" indicating both the atrium and ventricle. The second letter of the code identifies the chamber wherein cardiac activity is sensed, using the same letters to identify the atrium or ventricle or both, and wherein a "0" indicates no sensing takes place.

The third letter of the code identifies the action or response that is taken by the pacemaker. In general, three types of action or responses are recognized: (1) an Inhibiting ("I") response wherein a stimulation pulse is delivered to the designated chamber after a set period of time unless cardiac activity is sensed during that time, in which case the stimulation pulse is inhibited; (2) a Trigger ("T") response wherein a stimulation pulse is delivered to a prescribed chamber of the heart a prescribed period after a sensed event; (3) or a Dual ("D") response wherein both the Inhibiting mode and Trigger mode are evoked, inhibiting in one chamber of the heart and triggering in the other.

Thus, for example, a DVI pacemaker is a pacer (note that throughout this application, the terms "pacemaker" and "pacer" may be used interchangeably) that paces in both chambers of the heart, but only senses in the ventricle, and that operates by inhibiting stimulation pulses when prior ventricular activity is sensed. Because it paces in two chambers, it is considered as a dual chamber pacemaker. A VVI pacer, on the other hand, is a pacer that paces only in the ventricle and senses only in the ventricle. Because only one chamber is involved, it is classified as a single chamber pacemaker. It should be noted that most dual chamber pacemakers can be programmed to operate in a single chamber mode.

Much has been written and described in the art about the various types of pacemakers and the advantages and disadvantages of each. For example, reference is made to U.S. Pat. No. 4,712,555, to Thornander et al., co-invented by the present applicant, wherein some helpful background information about pacemakers and the manner in which they interface with a patient's heart is presented. This patent is hereby incorporated herein by reference.

One of the most versatile programmable pacemakers available today is the DDD pacemaker. This pacer represents a fully automatic pacemaker which is capable of sensing and pacing in both the atrium and ventricle. When functioning properly, the DDD pacer represents the dual chamber pacemaker with the least number of drawbacks. It is typically implanted in patients in an effort to maintain AV synchrony while providing bradycardia support.

In general, DDD pacing has four functional states: (1) P-wave sensing, ventricular pacing (PV); (2) atrial pacing, ventricular pacing (AV); (3) P-wave sensing, R-wave sensing (PR); and (4) atrial pacing, R-wave sensing (AR). Advantageously, for the patient with complete or partial heart block, the PV state of the DDD pacer tracks the atrial rate, which rate is set by the heart's S-A node, and then paces in the ventricle at a rate that follows this atrial rate. Because the rate set by the S-A node represents the rate at which the heart should beat in order to meet the physiologic demands of the body, at least for a heart having a properly functioning S-A node, the rate maintained in the ventricle by such a pacemaker is truly physiologic.

Those skilled in the art have long recognized the advantages of using an atrial rate based pacemaker. For example, U.S. Pat. No. 4,624,260, to Baker, Jr., et al., discloses a microprocessor-controlled dual chamber pacemaker having conditional atrial tracking capability. Similarly, U.S. Pat. No. 4,485,818, to Leckrone et al., discloses a microprocessor-based pacer which may be programmed to operate in one of a plurality of possible operating modes, including an atrial rate tracking mode.

Unfortunately, in some instances, it is possible for a given patient to develop fast atrial rhythms which result from pathological tachycardias and fibrillation. In these cases, the DDD pacer will pace the ventricle in response to the sensed atrial disrhythmia up to the programmed maximum tracking rate. While this upper rate limit is designed into the pacemaker to protect the patient from being paced too fast, it is not desirable to pace at the maximum upper rate limit for a long period of time, else the heart cannot efficiently perform its function of pumping blood through the body.

Therefore, attempts have been made in the art to prevent such atrial arrhythmias from developing. For example, U.S. Pat. No. 4,722,341, to Hedberg et al., teaches an atrium-controlled pacemaker wherein the pacemaker temporarily switches from an atrial rate based mode to a non-atrial rate based mode for a fixed number of stimulation pulses if the sensed atrial activity indicates an atrial arrhythmia may be developing. Unfortunately, however, for some patients, a temporary switching from one mode to another may not be sufficient to correct or arrest the arrhythmia.

What is needed is an atrial rate based pacemaker which will not only sense the atrial arrhythmia once it develops, but which will also take whatever corrective action is needed, for however long (i.e., not just temporarily), to prevent the heart from being paced at the maximum upper limit for long periods of time.

It is known that the dual chamber pacemaker itself may undesirably support (and even induce) some cardiac arrhythmias. This process is described, for example, in U.S. Pat. No. 4,788,980, to Buchanan et al., where such arrhythmias are referred to as a pacer mediated tachycardia, or PMT. The referenced patent discloses a particular technique for recognizing a PMT and terminating it once it develops. Similarly, U.S. Pat. No. 4,712,556, to Baker, proposes another technique for identifying PMT's, and proposes yet another technique for terminating such PMT. Still another patent, U.S. Pat. No. 4,554,921, to Boute et al., teaches modifying the atrial refractory period of the pacemaker in an attempt to break or terminate a PMT.

Regardless of the source of the arrhythmia, however, whether caused by a PMT or by other factors, if left unchecked, the DDD pacer will track the fast atrial rate and pace the ventricles up to the maximum tracking rate for a long period of time, resulting in low cardiac output. What is needed, therefore, is a method or technique for preventing an atrial rate based pacemaker from pacing the heart at the maximum pacing rate for prolonged periods of time, even when an atrial arrhythmia is present.

Sometimes it is possible at the time of implant of a pacemaker to determine whether an atrial fibrillation, atrial flutter, or atrial tachycardia condition is going to develop. In such instances, the pacemaker may always be programmed to operate in a different mode of operation, the leads may be repositioned within the heart, or other actions may be taken to minimize the likelihood of such arrhythmias occurring. Unfortunately, however, it is not always possible at the time of implant to determine whether a patient will develop an arrhythmia as a result of pacing.

Therefore, if such arrhythmias subsequently occur, they must be treated using other techniques, such as through the administration of drugs. Needless to say, the administration of drugs requires the attendance of a physician. Unfortunately, however, a physician is not always present when such arrhythmias develop, and even when a physician is available, such drugs undesirably also suppress the ability of the S-A node to increase the sinus rate during periods of exercise, emotional stress, or other physiologic stress. Thus, the use of such drugs effectively prevents the pacer from functioning as a true physiologic rate-responsive pacer.

What is needed is an approach for dealing with arrhythmias which develop after implant without necessitating the attendance of a physician and without compromising the pacer's ability to function as a physiologic rate-responsive pacer.

It is also possible that the atrial arrhythmia may be caused by the pacemaker's inability to sense P-waves. In such an instance, the paced competition with the native atrial activity may precipitate an atrial tachycardia or fibrillation. This inability to sense P-waves may be caused by numerous factors, but is usually caused by electrode dislodgement or movement, tissue growth, or other events which may occur several days or weeks after implant.

The ability of the pacemaker to sense P-waves is referred to as atrial sensitivity. At implant, the atrial sensitivity is adjusted based on various tests in order to ensure that P-waves are sensed with an adequate margin of safety. However, even this margin of safety may disappear over time, and it thus becomes necessary for a physician to reprogram the atrial sensitivity so that P-waves will be sensed. However, until reprogramming of the atrial sensitivity takes place, there is some possibility that P-waves will not be sensed, resulting in the undesirable atrial arrhythmias described above.

Thus, what is needed is a pacemaker which includes means for periodically checking, and adjusting as required, the atrial sensitivity, thereby assuring that P-waves will always be sensed by the pacemaker. U.S. Pat. No. 4,708,144, to Hamilton et al., represents one approach known in the art for automatically controlling the sensitivity of the pacemaker.

Further, with an atrial rate based dual chamber pacemaker, there is always the problem that a sustained activity period of the patient, resulting in a naturally high sinus rate, may be interpreted by the pacemaker as a pathological atrial arrhythmia. Hence, an atrial rate based pacemaker needs to incorporate some means to readily distinguish a sustained pathological atrial arrhythmia from a sustained activity period, and take appropriate action in each instance.

Advantageously, the pacemaker described herein, including the method of operating such pacemaker, addresses the above and other needs.

SUMMARY OF THE INVENTION

The disadvantages and limitations of the background art discussed above are overcome by the present invention. With this invention, an atrial rate based programmable pacemaker is provided which advantageously includes means for preventing the heart from being paced at the upper rate limit of the pacemaker for prolonged periods of time in the event the atrial rate exceeds a prescribed upper rate limit. The pacemaker includes means for operating in a prescribed dual chamber mode of operation, such as DDD, wherein the heart is paced at a rate that follows or tracks the atrial rate up to the upper rate limit of the pacemaker. When the atrial rate exceeds the upper rate limit, the pacemaker stimulates the heart at the upper rate limit, but also continues to monitor the atrial rate.

If the monitored atrial rate exceeds a second upper rate limit, e.g., a tachycardia rate limit, a pathological atrial arrhythmia or tachycardia condition is deemed to exist, and the pacemaker automatically switches from its existing mode of operation to an alternate mode of operation, e.g., a single chamber mode of operation. This mode switching is performed for the purpose of breaking or terminating the fast atrial condition. While in the alternate mode of operation, the atrial and/or ventricular rate continues to be monitored, and as soon as the rate drops to an acceptable level, the pacemaker automatically switches back to its initial atrial rate based mode.

In one embodiment of the invention, an external physiological sensor may optionally be utilized in the pacemaker to control the pacing rate of the pacemaker in the alternate pacing mode. This action ensures that the pacemaker is attempting to pace the heart at an appropriate heart rate based on the patient's actual physiologic needs at a time when the heart may be beating at an excessive rate, e.g., during a tachycardia or other arrhythmia. As with the first embodiment, as soon as the atrial or ventricular rate drops to an acceptable level, the pacemaker automatically switches back to its initial mode of operation.

In a still further embodiment, the pacemaker includes means for periodically verifying that atrial sensing is occurring. If a determination is made that atrial sensing is not occurring, an adjustment mode is initiated during which the sensitivity of the atrial channel is automatically adjusted, as required.

It is thus a feature of the present invention to provide a programmable pacemaker which prevents the heart from being paced at the maximum rate of the pacemaker for prolonged periods of time. It is a further feature of the invention to provide such a pacemaker wherein the pacemaker continues to sense the rate of cardiac activity even when that rate exceeds the upper rate limit of the pacemaker.

Yet another feature of the invention is to provide such a pacemaker wherein the mode of operation of the pacer automatically switches from a first mode to a second mode in the event the sensed cardiac activity exceeds a prescribed second upper limit, this second upper limit being above the pacemaker's normal upper rate limit. While in this second mode of operation, an additional feature of the invention provides for the continued sensing of the prescribed cardiac activity and the automatic switching of the pacemaker back to its first mode of operation as soon as the prescribed cardiac activity returns to a normal level.

Still another feature of the invention provides such an automatic mode switching pacemaker wherein the pacing rate of the pacemaker while in its second mode of operation is controlled by an external physiological sensor, such as an activity sensor. A still further feature of the invention provides a programmable pacemaker wherein the sensitivity of the sense amplifier(s) used to sense cardiac activity may be automatically adjusted at prescribed times or intervals. Finally, all of the aforesaid advantages and objectives are achieved without incurring any substantial relative disadvantage.

DESCRIPTION OF THE DRAWINGS

These and other advantages of the present invention are best understood with reference to the drawings, in which:

FIGS. 4A and 4B are flow chart diagrams illustrating the operation of the pacemaker of FIG. 1.

DETAILED DESCRIPTION OF THE PREFERRED EMBODIMENT

Figure 1:
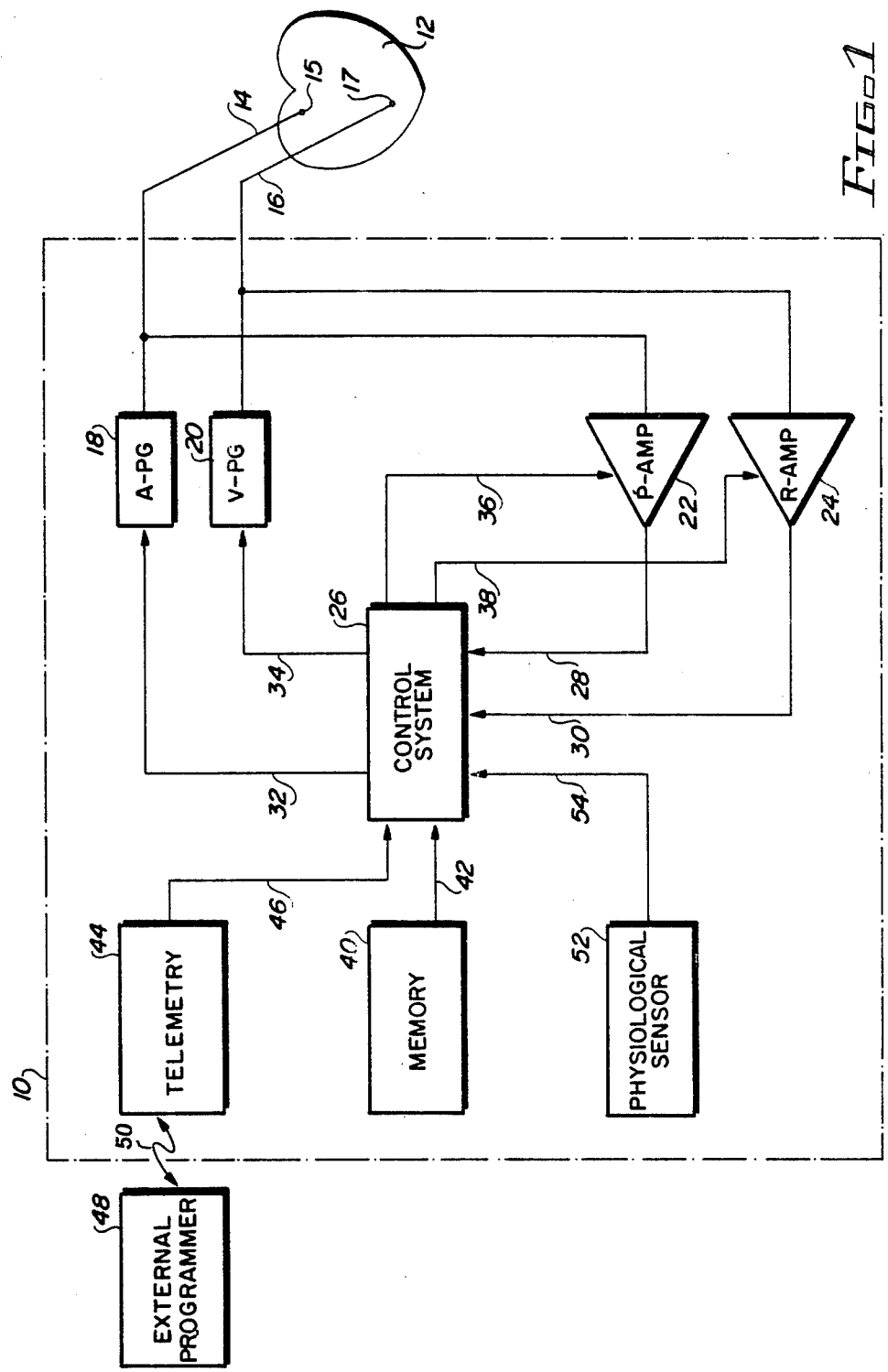
FIG. 1 is a block diagram of a dual chamber programmable pacemaker.

The following description is of the best presently contemplated mode of practicing the invention. This description is not to be taken in a limiting sense but is made merely for the purpose of describing the general principles of the invention. The scope of the invention should be ascertained with reference to the appended claims.

Before describing the invention in more detail, a brief review of cardiac physiology may be helpful. Essentially, the heart is a pump which pumps blood throughout the body. It consists of four chambers, two atria and two ventricles. In order to efficiently perform its function as a pump, the atrial muscles and ventricular muscles must contract in a proper sequence and timed relationship.

In a given cardiac cycle (corresponding to one "beat" of the heart), the two atria contract, forcing the blood therein into the ventricles. A short time later, the two ventricles contract, forcing the blood therein to the lungs (right ventricle) or through the body (left ventricle). Meanwhile, blood from the body fills up the right atrium and blood from the lungs fills up the left atrium, waiting for the next cycle to begin. A typical healthy adult heart may beat at a rate of 60-70 beats per minute (bpm) while at rest, and may increase its rate to 140-180 bpm when the adult is engaging in strenuous physical exercise, or undergoing other physiologic stress.

The healthy heart controls its own rhythm naturally from its S-A node, located in the upper portions of the right atrium. The S-A node generates an electrical impulse at a rate commonly referred to as the "sinus" rate. This impulse is delivered to the atrial tissue when the atria are to contract; and, after a suitable delay (on the order of 40-80 milliseconds), is delivered to the ventricular tissue when the ventricles are to contract.

When the atria contract, a detectable electrical signal referred to as a P-wave is generated. When the ventricles contract, a detectable electrical signal referred to as an R-wave is generated. The R-wave is much larger than the P-wave, principally because the ventricular muscle tissue is much more massive than is the atrial muscle tissue. The atrial muscle tissue need only produce a contraction sufficient to move the blood a very short distance, from the respective atrium to its corresponding ventricle. The ventricular muscle tissue, on the other hand, must produce a contraction sufficient to push the blood over a long distance, e.g., through the complete circulatory system of the entire body.

Other electrical signals or waves are also detectable within a cardiac cycle, such as a Q-wave (which immediately precedes an R-wave), an S-wave (which immediately follows an R-wave), and a T-wave (which represents the repolarization of the ventricular muscle tissue).

It is the function of a pacemaker to provide electrical stimulation pulses to the appropriate chamber(s) of the heart (atria or ventricles) in the event the heart is unable to beat on its own, i.e., in the event either the S-A node fails to generate its own natural stimulation pulses at an appropriate sinus rate, or in the event such natural stimulation pulses are not delivered to the appropriate cardiac tissue. Most modern pacemakers accomplish this function by operating in a "demand" mode wherein stimulation pulses from the pacemaker are provided to the heart only when it is not beating on its own, as sensed by monitoring the appropriate chamber of the heart for the occurrence of a P-wave or an R-wave. If a P-wave or an R-wave is not sensed within a prescribed period of time (which period of time is most often referred to as the "escape interval"), then a stimulation pulse is generated at the conclusion of this prescribed period of time and delivered to the appropriate heart chamber via a pacemaker lead.

Further details associated with cardiac physiology and the operation of the heart as controlled or monitored by a pacemaker may be found in U.S. Pat. No. 4,712,555, to Thornander et al., which patent was incorporated by reference above.

Referring now to FIG. 1, a simplified block diagram of a dual chamber pacemaker 10 is illustrated. The pacemaker 10 is coupled to a heart 12 by way of leads 14 and 16, the lead 14 having an electrode 15 which is in contact with one of the atria of the heart, and the lead 16 having an electrode 17 which is in contact with one of the ventricles of the heart. The leads 14 and 16 carry stimulating pulses to the electrodes 15 and 17, respectively, from an atrial pulse generator (A-PG) 18 and a ventricular pulse generator (V-PG) 20, respectively.

Further, electrical signals from the atria are carried from the electrode 15, through the lead 14, to the input terminal of an atrial channel sense amplifier (P-AMP) 22. Electrical signals from the ventricles are carried from the electrode 17, through the lead 16, to the input terminal of a ventricular sense channel amplifier (R-AMP) 24.

Controlling the dual chamber pacer 10 is a control system 26. The control system 26 receives the output signals from the atrial amplifier 22 over a signal line 28. Similarly, the control system 26 receives the output signals from the ventricular amplifier 20 over a signal line 30. These output signals are generated each time that a P-wave or an R-wave is sensed within the heart 12.

The control system 26 also generates trigger signals which are sent to the atrial pulse generator 18 and the ventricular pulse generator 20 over two signal lines 32 and 34, respectively. These trigger signals are generated each time that a stimulation pulse is to be generated by the respective pulse generator 18 or 20. The atrial trigger signal is referred to simply as the "A-pulse", and the ventricular trigger signal is referred to as the "V-pulse".

During the time that either an A-pulse or V-pulse is being delivered to the heart, the corresponding amplifier, P-AMP 22 or R-AMP 24, is typically disabled by way of a blanking signal presented to these amplifiers from the control system over signal lines 36 and 38, respectively. This blanking action prevents the amplifiers 22 and 24 from becoming saturated from the relatively large stimulation pulses which are present at their input terminals during this time. This blanking action also helps prevent residual electrical signals present in the muscle tissue as a result of the pacer stimulation from being interpreted as P-waves or R-waves.

Still referring to FIG. 1, the pacer 10 also includes a memory circuit 40 which is coupled to the control system 26 by a suitable data/address bus 42. This memory circuit 40 allows certain control parameters, used by the control system 26 in controlling the operation of the pacemaker, to be programmably stored and modified, as required, in order to customize the operation of the pacer 10 to suit the needs of a particular patient. Further, data sensed during the operation of the pacer 10 may be stored in the memory 40 for later retrieval and analysis.

A telemetry circuit 44 is further included in the pacer 10. This telemetry circuit 44 is connected to the control system 26 by way of a suitable command/data bus 46. In turn, the telemetry circuit 44, which is included within the implantable pacer 10, may be selectively coupled to an external programming device 48 by means of an appropriate communication link 50, which communication link 50 may be any suitable electromagnetic link, such as an RF (radio frequency) channel.

Advantageously, through the external programmer 48 and the communication link 50, desired commands may be sent to the control system 26. Similarly, through this communication link 50 and the programmer 48, data (either held within the control system 26, as in a data latch, or stored within the memory 40,) may be remotely received from the pacer 10. In this manner, non-invasive communications may be established with the implanted pacer 10 from a remote, non-implanted, location.

The pacer 10 in FIG. 1 is referred to as a dual chamber pacemaker because it interfaces with both the atria and the ventricles of the heart. Those portions of the pacer 10 which interface with the atria, e.g., the lead 14, the P-wave sense amplifier 22, the A-pulse generator 18, and corresponding portions of the control system 26, are commonly referred to as the atrial channel. Similarly, those portions of the pacer 10 which interface with the ventricles, e.g., the lead 16, the R-wave sense amplifier 24, the V-pulse generator 20, and corresponding portions of the control system 26, are commonly referred to as the ventricular channel.

In accordance with one embodiment of the present invention, the pacemaker 10 further includes a physiological sensor 52 which is connected to the control system 26 of the pacer over a suitable connection line 54. While this sensor 52 is illustrated in FIG. 1 as being included within the pacer 10, it is to be understood that the sensor 52 may also be external to the pacer 10, yet still be implanted within or carried by the patient.

A common type of sensor 52 is an activity sensor, such as a piezoelectric crystal, which is mounted to the can or case of the pacemaker. Other types of physiologic sensors are also known, such as sensors which sense the oxygen content of blood, respiration rate, pH of blood, body motion, and the like. The type of sensor used is not critical to the present invention. Any sensor which is capable of sensing some physiological parameter which is relatable to the rate at which the heart should be beating may be used.

Such sensors are commonly used with "rate-responsive" pacemakers in order to adjust the rate (escape interval) of the pacer in a manner which tracks the physiological needs of the patient. In accordance with one embodiment of the present invention, the sensor 26 is used to control the escape interval or pacing rate of the pacer 10 when the pacer 10 is operating in an alternate mode of operation other than an atrial rate based mode of operation. This is described more fully below in connection with the description of FIG. 4A.

Figure 2:
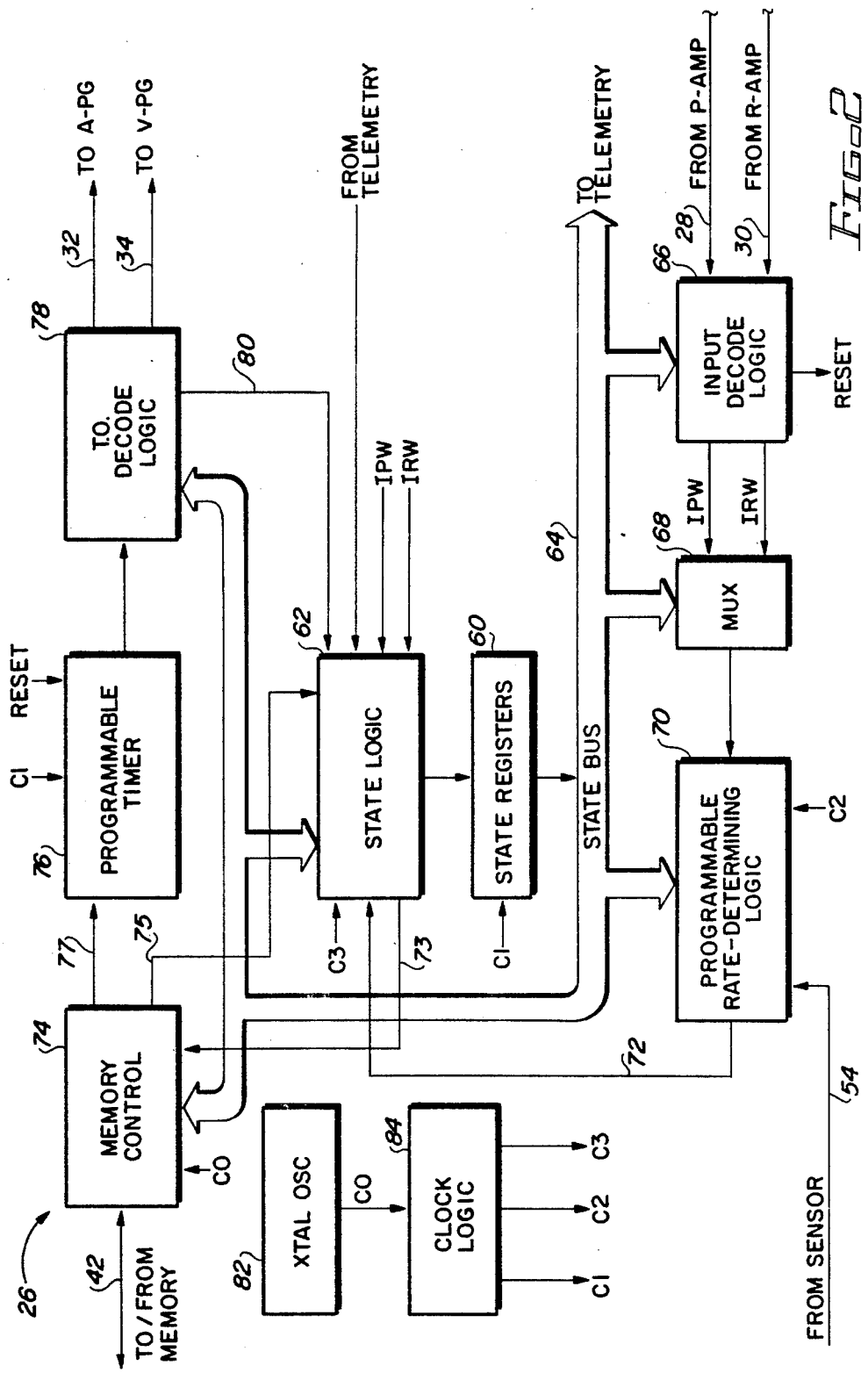
FIG. 2 is a block diagram of one possible embodiment of the control logic of the pacemaker of FIG. 1.

Referring next to FIG. 2, a block diagram of one embodiment of the control system 26 of the pacer 10 is illustrated. It is noted that other embodiments of a control system 26 may also be utilized, such as a microprocessor-based control system. A representative microprocessor-based system is described, for example, in copending U.S. patent application No. 07/301,934, filed Jan. 25, 1989, entitled "Microprocessor Controlled Rate-Responsive Pacemaker Having Automatic Rate Response Threshold Adjustment", assigned to the same assignee as is the present application. This patent application is hereby incorporated herein by reference.

The control system shown in FIG. 2 is based on a state machine wherein a set of state registers 60 define the particular state of the pacer 10 at any instant in time. In general, and as an overview of state machine operation, each state, by design, causes a certain activity or function to be carried out. Several states are executed in a sequence during a given cardiac cycle. The sequence of states which is executed in a particular cardiac cycle is determined by the particular events which occur, such as the sensing of a P-wave or an R-wave, as well as the current state, as certain states can only be entered from certain other states.

Only one state may exist at any instant of time, although several different state machines (or control systems) may operate in parallel to control diverse functions. For example, the telemetry circuit 44 (FIG. 1) preferably utilizes its own state machine, such as is described in the above-cited copending patent application. This telemetry circuit state machine operates essentially independently of the control system state machine shown in FIG. 2.

At the heart of the control system 26 is the state logic 62. It is the state logic which controls the "state" of the state registers 60, and hence the function or operation which will next be carried out by the system. The state logic 62 receives as inputs the current state of the state registers 60, made available over a state bus 64 (which state bus 64 directs the state of the system to several sections of the control system), as well as other signals indicating the current status of the system or events which have occurred.

The output signals from the P-AMP 22 (FIG. 1) and the R-AMP 24 (FIG. 1) are directed to an input decode logic circuit 66. The input decode logic circuit 66 generates appropriate logic signals "IPW" (Inhibiting P-Wave) and "IRW" (Inhibiting R-Wave) which are selected by a multiplexer 68 and sent to rate-determining logic 70. These signals are also sent to the state logic 62. The function of the rate-determining logic 70 is to determine the rate at which either the IPW or IRW signals are occurring.

A signal representative of this rate is sent, as an output signal from the rate determining logic 70, to the state logic 62 over a signal line 72. The rate-determining logic 70 further receives a sensor rate signal from the sensor 52 (FIG. 1), and (depending upon the particular state of the system, as defined by the state registers 60, and as made available to the rate-determining logic 70 over the state bus 64) sends a rate signal to the state logic 62 over signal line 72 indicative of this sensor rate.

Still referring to FIG. 2, a memory control circuit 74 provides the needed interface between the circuits of the control system 26 and the memory 40 (FIG. 1). This memory control circuit 74 may be any conventional memory access circuit which sends or receives data to or from memory at a specified address. Data retrieved from the memory 40 may be sent to either the state logic 62 over signal line(s) 75 or to a programmable timer 76 over a signal line(s) 77. Data sent to the memory 40 may be either the current state of the system (obtained off of the state bus 64), or other selected signals from the state logic 62 (as made available over signal line(s) 73).

The function of the programmable timer 76 is to define a prescribed time interval, the length of which is set by the signal(s) received from the memory control 74 over the signal line(s) 77, and the starting point of which begins coincident with the start of the current state, as obtained from the state bus 64. The timer 76 further generates a time-out (T.O.) signal when this prescribed time interval has elapsed.

During this prescribed time interval, the timing function may be reset by a reset signal, typically obtained from the input decode logic 66, although some states (as obtained from the state bus 64) may also effectuate an immediate reset of the timer 76. The time-out signal is sent to a time-out decode logic 78. It is the function of the time-out decode logic 78 to generate the appropriate trigger signals which are sent to the A-pulse generator 18 or the V-pulse generator 20 (FIG. 1). Further, an appropriate logic signal(s) is sent to the state logic 62 by the time-out decode logic 78 over the signal line(s) 80 in order to notify the state logic 62 that the respective trigger signals have been generated.

An oscillator 82, preferably a crystal-controlled oscillator, generates a basic clock signal C0 which controls the operation of the system logic. This clock signal C0 is sent to clock logic circuits 84, where other appropriate clock signals, such as clock signals C1, C2, and C3, are generated, all derived from the basic clock signal C0. These clock signals are distributed throughout the control system 26 in order to appropriately synchronize the various events and state changes which occur within the pacemaker.

The rate of the basic clock signal C0 is not critical to the present invention. In general, a rate of 25-40 Khz for the basic clock rate C0 is adequate. This rate provides a basic time increment of 25-40 microseconds each clock cycle, and this is more than enough time to effectively control the pacemaker operation. If desired, a faster basic clock rate may be used, particularly by the memory control 74, to speed up the data transfer between the control system 26 and the memory 40, although for most pacemaker operations, a fast data transfer rate is not essential.

In operation, the control system of FIG. 2 starts at an initial state, wherein the state registers 60 assume a prescribed value which defines the initial state. For example, assuming four flip-flops are used for the state registers 60, an initial state might be "1000" (hexadecimal "8") wherein the first flip-flop assumes a "1" state, and the remaining three flip-flops each assume a "0" state. This state may be defined as a V-A Delay (VAD) state wherein a prescribed VA interval is initiated. This interval may be considered as the "escape interval" mentioned previously.

As soon as the memory control 74 detects that the VAD state has been initiated, as evidenced by the "1000" appearing on the state bus 64, it retrieves from the memory 40 an appropriate data word, previously programmed into the memory 40 from the external programmer 48, which defines the desired length of the V-A delay. This data word is sent to the programmable timer and sets the length of the time period which is to be measured during the VAD state.

The timer 76 is essentially just a counter which counts down (or counts up), using a specified clock signal, to the value specified in the data word. When the counting has been completed, and assuming that the counter has not been reset by the occurrence of a P-wave or an R-wave, the counter or timer 76 is said to have "timed-out", and an appropriate time-out signal is generated which is sent to the time-out decode logic 78.

The decode logic 78, in turn, recognizes that the current state of the system is the VAD state (as determined by monitoring the state bus 64), and therefore that the VA interval (escape interval) has timed out without any cardiac activity having been sensed, generates an A-pulse trigger signal, sent to the A-pulse generator 18, so that the atrium can be stimulated. At the same time, an appropriate logic signal(s) is sent to the state logic 62 over the signal line(s) 80 to alert the state logic to the fact that the timer 76 has timed out.

The state logic 62, in response to receiving the signal(s) from the time-out decode logic 78, and also in response to the current VAD state, triggers the next state of the prescribed sequence. For DDD operation, this state is typically a blanking state, or BLANK state, during which the P and R sense amplifiers, 22 and 24, are disabled. Accordingly, the state logic generates appropriate signal(s) on signal lines 36 and 38 to blank the P-wave sense amplifier 22 and the R-wave sense amplifier 24, respectively, and also causes the state registers 60 to change to a BLANK state, which state could be defined, for example, by the flip-flops of the state registers 62 assuming a "0001" (hex "1") condition.

This BLANK state, detected on the state bus 64, causes the memory control circuitry 74 to retrieve an appropriate data word from the memory 40 which defines the length of the blanking interval, which data word is loaded into the programmable timer 76. As soon as the timer 76 times out, indicating that the prescribed blanking interval has elapsed, a time-out signal is generated which is sent to the time-out decode logic 78. Upon receipt of this time-out signal, and in response to the current state being a BLANK state, the time-out decode logic 78 sends an appropriate logic signal to the state logic 62. The state logic 62 responds by steering the state registers 62 to assume the next state in the prescribed sequence, which may be, for example, an A-V Delay (AVD) state.

At the beginning of the AVD state, another value is loaded into the programmable timer 76 which defines the length of the AV interval. If the timer 76 times out without being reset, indicating that no P-waves or R-waves have been sensed, the decode logic 78 generates a V-pulse trigger signal, and notifies the state logic 62 of this event. The state logic 62, in turn, causes the next appropriate state to be entered, which state may be another blanking state, or BLANK state, similar to the one described above, but having perhaps a different duration. At the conclusion or timing out of this second BLANK state, the next state in the prescribed sequence is initiated, which state may be a refractory (REF) state.

In the manner described above, the control system 26 assumes one state after another, thereby controlling the operation of the pacemaker 10. In general, a state is changed when the timer 76 times out, or when a prescribed event occurs. For example, if during the VAD state an IPW signal is received (indicating that a P-wave has been sensed), the input decode logic 66 generates a reset signal to reset the timer 76, and the state logic 62 responds by immediately (typically within the next few clock cycles) changing the state to the next appropriate state, for example, an AVD state.

Further, if during the AVD state an IRW signal is received (indicating that an R-wave has been sensed), the input decode logic 66 generates another reset signal to reset the timer 76, and the state logic responds by immediately changing the state to the next appropriate state, for example, a refractory (REF) state. It is noted that the state of the control system 26 could also be changed by receipt of an appropriate command from the telemetry system.

The control system 26 of FIG. 2 may be realized using dedicated hardware circuits, or by using a combination of hardware and software (or firmware) circuits. The appropriate sequence of states for a given mode of operation, such as DDD or VVI, for example, may be defined by appropriate control of the memory control 74 and the state logic 62. These circuit elements, in turn, are most easily controlled through an appropriate software or firmware program which is placed or programmed into the pacemaker memory circuits. The manner of accomplishing such programming is well known in the art.

A detailed description of the various circuits of the control system 26 of FIG. 2 will not be presented herein because all such circuits may be conventional, or may be patterned after known circuits available in the art. Reference is made, for example, to the above incorporated by reference U.S. Pat. No. 4,712,555, to Thornander et al., wherein a state-machine type of operation for a pacemaker is described; and to U.S. Pat. No. 4,788,980, to Buchanan et al., wherein the various timing intervals used within the pacemaker and their interrelationship are more thoroughly described.

It is noted that a dual chamber programmable pacemaker may have up to eighteen states associated with its control system. These states are described fully in the above-referenced patent application. A summary of these states is presented below in Table 1.

TABLE 1

| | States of the Pacemaker Control System | |
|---|---|---|
| State | Symbol | Description |
| 0 | APW | A-Pulse (A-Pulse triggered) |
| 1 | BLANK | V-Sense Input Inhibit (Blank) |
| 2 | AREF | A Refractory |
| 3 | SIPW | Sensed Inhibiting P-wave (P-wave sensed) |
| 4 | AVD | A-V Delay |
| 5 | CROSS | Crosstalk Sense |
| 6 | VPW | V-Pulse (V-Pulse triggered) |
| 7 | STRW | Sensed Inhibiting R-wave (R-wave sensed) |
| 8 | VAD | V-A Delay |
| 9 | SHORT1 | Shorten A-V Delay a first prescribed amount if IPW during SHORT1 with Physiologic A-V Delay On |
| A | MTR | Max Track Rate |
| B | SHORT2 | Shorten A-V Delay a second prescribed amount if IPW during SHORT2 with physiologic A-V Delay On |
| C | RRT | Lengthen VA interval if at low battery |
| D | RNOISE | R Noise sensed during VREF or RNOISE |
| E | LIPW | Latched IPW - P-wave sensed in MTR |
| F | PNOISE | P Noise sensed during AREF or PNOISE |
| (none) | VREF | V Refractory, independent 1-bit state machine synchronized to pulse generator when AREF starts |
| (none) | ABSREF | Absolute Refractory for a prescribed period, starts when AREF starts |

In addition to the states identified in Table 1, the present invention preferably incorporates two additional states: (1) an ARC (Atrial Rate Check) state, and an ARV (Atrial Rate Verify) state. At least the ARV state is preferably defined by an independent 1-bit state machine which operates in parallel with the system state machine.

Figure 3:
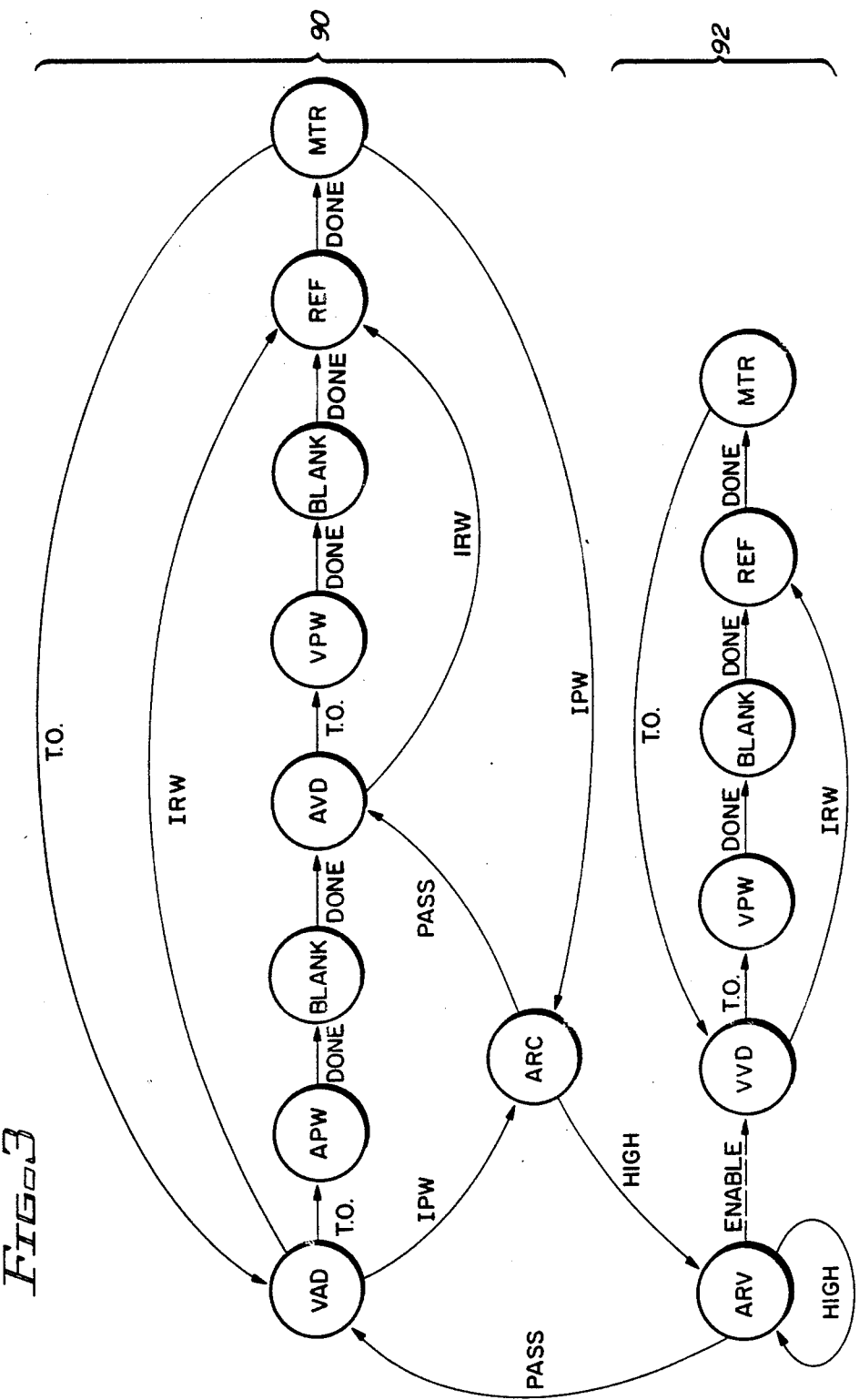
FIG. 3 is a simplified state diagram of the pacemaker of FIG. 1 when operating in accordance with one embodiment of the present invention.

The operation of the pacemaker control system 26 of FIGS. 1 and 2 as it relates to the present invention may be better understood by reference to the state diagram of FIG. 3. The state diagram of FIG. 3 illustrates in each circle a particular state which the system may assume. The connecting lines between the circles illustrate the various events which may cause the state to change.

Before explaining FIG. 3, however, it should be emphasized that FIG. 3 depicts a simplified state diagram. That is, for purposes of clarity only a portion of the states shown in Table 1 are used by the pacemaker represented by FIG. 3. Further, some of the states which may be used in the pacemaker, as identified in Table 1, such as the absolute refractory state, ABSREF, the ventricular refractory state, VREF, and the atrial refractory state, AREF, are combined in the pacemaker state diagram of FIG. 3 as simply a refractory state, REF. This is done for simplicity of explanation because the various responses which may be taken by the pacemaker during the AREF or VREF states, for example, to better distinguish noise from other events, may remain unchanged for the present invention.

In other words, for purposes of understanding the present invention it is sufficient to assume that during a refractory period or state no action is taken until the refractory state, REF, times out, and the next state is entered. Other states identified in Table 1, such as the CROSS, RRT, RNOISE, LIPW, SHORT1 and SHORT2 states are not included in the description which follows because they play no part in the invention. In fact, for purposes of the present invention, a pacemaker may function without these states.

Other states shown in Table 1, such as the SIPW and SIRW states, are referred to in the state diagram of FIG. 3 as "events" (IPW and IRW) which simply trigger the state of the control system to shift from one state to another. In practice, a logic designer may choose to define a temporary state, such as an SIPW or SIRW state, to indicate that a P-wave or an R-wave has been detected by receipt of an IPW or IRW signal. However, for purposes of understanding the present invention, it is sufficient to simply recognize that the sensing of a P-wave (IPW) or the sensing of an R-wave (IRW) is an event which can affect (change) the state of the control system.

Referring then to the state diagram of FIG. 3, the operation of the present invention will be described. As has been indicated, the present invention is directed to a particular manner of controlling or operating a pacemaker which is operating in an atrial rate based mode, such as DDD. The bracketed portion 90 of FIG. 3 essentially represents a simplified state diagram of a DDD pacer. That is, a VAD state is entered.

If a timeout occurs without a P-wave being sensed, then an APW state is entered during which an A-pulse is delivered to the atrium, followed by a BLANK state, followed by an AVD state. If the AVD state times out without an R-wave being sensed, then a VPW state is entered during which a V-pulse is delivered to the ventricle, followed by a BLANK state, followed by a refractory, or REF, state, followed by a maximum tracking rate (MTR) state. If the MTR state times out without a P-wave being sensed, then the VAD state is reinitiated.

Assuming that no P-waves or R-waves are sensed, the above cycle repeats itself with an A-pulse being generated after every VAD state and a V-pulse being generated after every AVD state. Notice that the MTR state assures that these stimulation pulses will not be delivered at a rate which exceeds a maximum upper limit (which upper limit is programmable). That is, the MTR state inserts a known time delay into the sequence of states which separates the A-pulse and the V-pulse by a set time period. In effect, this set time period defines a maximum upper rate limit (URL) at which the heart can be paced by the pacemaker. Advantageously, this set time period can be programmed to any desired value, thereby allowing the URL to be programmably selected.

In accordance with conventional DDD operation, if a P-wave is sensed (IPW) during either the VAD or MTR states, the AVD state is entered. The present invention modifies this operation by inserting an intermediate state, identified as an ARC (Atrial Rate Check) state, into the sequence. The ARC state is entered upon the occurrence of an IPW. During the ARC state, the atrial rate is checked or measured. This operation is carried out by the rate-determining logic 70 of FIG. 2, or its equivalent.

If the rate is below a prescribed threshold limit, hereafter a tachycardia rate limit (TRL), then the AVD state is entered, and the normal DDD operation continues. This tachycardia rate limit, or TRL, is set at a rate higher than the maximum upper rate limit, or URL, of the pacemaker. Thus, the ARC state is entered (that is, the atrial rate is checked or measured) even when the pacer is stimulating the heart at the URL. If during the ARC state a determination is made that the atrial rate exceeds the TRL (identified in FIG. 3 as a "HIGH" event), then an atrial rate verify (ARV) state is entered during which the atrial rate continues to be monitored.

The ARV state is maintained for so long as the atrial rate remains above a third prescribed rate threshold, referred to as $T_3$ herein. The sensing that the atrial rate exceeds $T_3$ during the ARV state is identified in FIG. 3 as a "HIGH" event.

During the ARV state, the pacemaker switches from the DDD mode of operation to an alternate mode of operation. This alternate mode of operation is preferably a non-atrial rate based mode, such as VVI. The bracketed portion 92 of the state diagram of FIG. 3 represents a simplified state diagram of a VVI pacer. So long as the pacer remains in the ARV state, the VVI mode (or other desired mode) is enabled and the pacer functions in a conventional VVI fashion (or other desired mode).

However, in the event a determination is made in the ARV state that the atrial rate has decreased to an acceptable level (which event is identified in FIG. 3 as a "PASS" event), that is, to a level less than the threshold $T_3$, then the pacemaker switches back to operate in the initial atrial rate based mode.

Figure 4A:
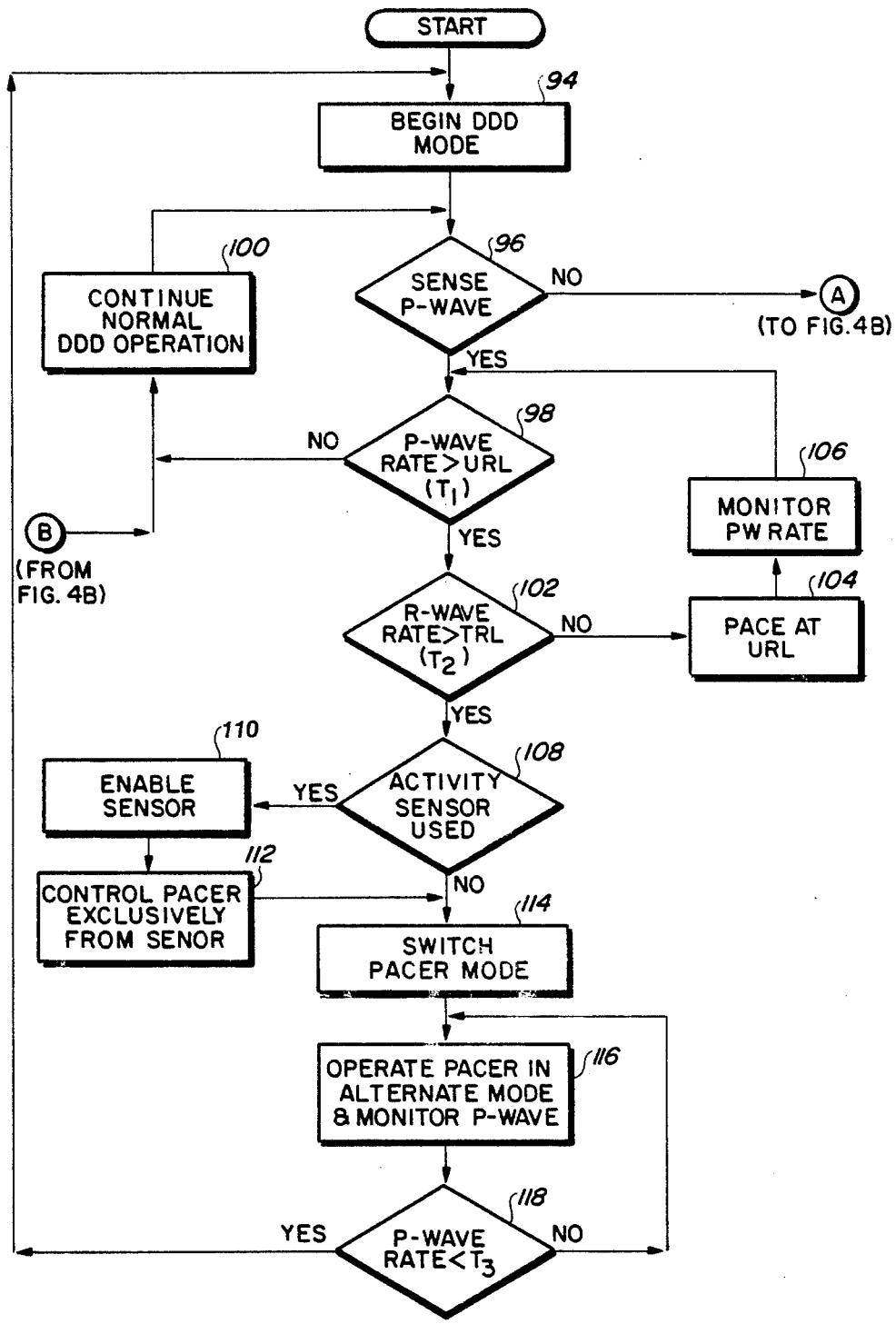

The above operation is further illustrated in the flow chart of FIG. 4A. As seen in FIG. 4A, the DDD mode of operation is initialized at block 94. During the normal DDD operation, a determination is made as to whether a P-wave has been sensed (block 96). If not, a determination is made as to whether the atrial channel sensitivity needs to be adjusted, as shown in the block diagram of FIG. 4B, explained below. If a P-wave is sensed, a determination is next made (block 98) as to whether the atrial rate (P-wave rate) exceeds a first rate limit threshold, $T_1$, which first rate limit is the upper rate limit (URL) of the pacemaker.

This operation is carried out by the rate-determining logic 70 (FIG. 2) using any suitable technique. Typically, atrial rate is determined by simply measuring the period or interval between successive P-waves, as described for example in U.S. Pat. No. 4,722,341, to Hedberg et al. Preferably, however, in accordance with the present invention, several P-waves are monitored, and an average P-rate value is obtained, or other rate measuring techniques are used (such as maintaining a running average of the P-waves over the last several cycles), thereby filtering out any abnormal or one-of-a-kind fast P-waves that may occasionally occur.

If the P-wave rate is less than the first threshold rate limit, $T_1$, then the pacemaker continues to operate in conventional DDD fashion (cycling back through block 100). If, however, the determination made at block 98 indicates that the atrial rate exceeds the first rate threshold $T_1$, a second determination is made (block 102) as to whether the atrial rate exceeds a second rate threshold value, $T_2$. This second rate threshold $T_2$ may be thought of as a tachycardia rate limit (TRL), and represents a programmable value indicative of the maximum P-wave rate that will be tolerated for a particular patient before action is taken to stop the fast atrial rate.

If the atrial rate is less than the TRL, or $T_2$, then the pacer continues to pace at the URL (block 104), and the P-wave continues to be monitored (cycling through block 106). If, however, a determination is made at block 102 that the atrial rate exceeds the TRL, then the pacer mode is switched from DDD to an alternate mode of operation (block 114), such as VVI or VVT.

Before switching to the alternate mode of operation, a determination is also made (block 108) as to whether an activity sensor, such as the sensor 52 (FIG. 2), is to be used with the pacer during its alternate mode of operation. If so, the sensor is enabled (block 110) and the control system of the pacemaker is modified appropriately so as to be controlled exclusively by the sensor (block 112). That is, the sensor provides a rate-determining signal which sets the value of the escape interval or pacing interval used by the pacer during its alternate mode of operation. In this manner, the pacer can better attempt to bring the heart under control by providing stimulation pulses only as dictated by the sensor, not as dictated by the arrhythmatic heart.

After the pacer has been switched to operate in the alternative mode of operation (block 114), the pacer continues to operate in this mode in conventional manner at the same time that the atrial rate is monitored (block 116). Periodically, e.g., every cardiac cycle, or every n cardiac cycles, where n is an integer greater than one, the atrial rate is again checked (block 118). If a determination is made that the atrial rate has dropped below a third prescribed rate threshold, $T_3$, then the pacer is switched back to its initial atrial rate based mode of operation (block 94).

The pacer continues to operate in this initial mode in accordance with the process described above, that is, as indicated by the flow chart of FIG. 4A. If the determination made at block 118 indicates that the atrial rate has not dropped below the threshold $T_3$, then the pacer continues to operate in the alternate mode of operation (block 116) in a conventional manner, except that the atrial rate continues to be monitored. During this time, the pacer is in the ARV state, as described above in connection with the state diagram of FIG. 3.

Typical values for the rate threshold limits $T_1$, $T_2$ and $T_3$ may be on the order of 150-180 bpm for $T_1$, 200-230 bpm for $T_2$, and 100-150 bpm for $T_3$.

Referring next to FIG. 4B, another feature of the present invention will be described. In the preferred embodiment of the present invention, this feature is included within the same pacer as are the mode switching features of FIG. 4A, and hence FIG. 4B is drawn as a continuation or extension of the flow chart of FIG. 4A. As previously indicated, sometimes it is the pacer's inability to sense a P-wave while operating in an atrial rate based mode which gives rise to a cardiac arrhythmia. Hence, it is desirable to determine whether P-waves are being sensed and, if not, to adjust the sensitivity of the P-wave sense amplifier so that they can be sensed. Thus, in FIG. 4A, one of the first determinations which is made (block 96) is whether a P-wave is sensed. If not, then the process described in FIG. 4B is invoked.

Upon entering the process of FIG. 4B, a decision is initially made as to whether the A-channel sensitivity is to be verified (block 120). This block is present in the flow chart simply to emphasize that A-channel sensitivity verification may be a selectable option programmed into the pacemaker. If the option is off—if the atrial channel sensitivity is not to be verified—then the process simply returns back to FIG. 4A and conventional DDD operation continues (block 100). If the option is on, then the pacer mode is switched to a test/verify mode (block 122).

In accordance with this special test/verify mode, the atrial channel is monitored for a prescribed period of time (block 124), such as 5-10 seconds, to determine if any P-waves are sensed (block 126). If P-waves are sensed, then the process makes a determination whether the test should be performed again (block 128). This determination (to test again) is preferably an option which can be programmed into the pacemaker at implant and later modified, as required, by the physician. For example, it may be desirable for a given patient to monitor the atrium for the prescribed period of time (block 124) for several consecutive time periods, e.g. five periods of 5-10 seconds each.

If a P-wave is regularly sensed during all of these time periods, then a final decision can be made at block 128 to terminate the test/verify mode. In such case, the pacer mode is switched back to DDD, or another initial atrial rate based mode, (through block 130) and the normal operation of the pacer for that mode continues (block 100). If however, a P-wave is not sensed during the prescribed time period, or is not regularly sensed during all of the time periods during which the test is performed, than such is an indication that the A-channel sensitivity probably needs to be adjusted.

It is noted that "atrial channel sensitivity" refers to the ability of the P-wave sense amplifier 22, FIG. 1, to sense P-waves. By adjusting the gain of this amplifier, which adjustment can be made using techniques known in the art, the magnitude of the P-waves which are detected by the amplifier may be optimally set.

Accordingly, for the case where P-waves are not being sensed, the sensitivity of the atrial sense amplifier is adjusted by a prescribed increment (block 132). Sensitivity settings are typically measured in millivolts, and this incremental adjustment is preferably on the order of 0.1-0.3 millivolts per increment. After making this incremental adjustment, another determination is made (block 134) as to whether P-waves are being sensed. If so, then this new sensitivity is maintained (block 136), the pacer is switched back to the DDD or other atrial rate based mode (block 138), and the normal operation of the pacer continues for that mode (block 100).

Where P-waves are not sensed at block 134, even after the sensitivity has been adjusted by the specified incremental amount, a determination is made as to whether further incremental adjustments of the sensitivity are possible (block 140). If so, then the next incremental adjustment is made and the process continues until a P-wave is sensed. If not, i.e., if there is no further adjustment range possible, then a major failure of the atrial channel exists, and the pacer immediately ceases its efforts to monitor P-waves and instead switches to monitoring R-waves (block 142).

If the R-wave rate is determined to be above a prescribed threshold (block 144), for example, above the TRL, then the heart is still experiencing a tachycardia or other arrhythmia and the pacer mode is immediately switched to a different mode of operation (block 146), as required, in order to break the tachycardia and to provide the safest possible mode of operation for the patient. For example, a VOO mode may be initiated (ventricular pacing, no sensing).

This "safe" mode of operation continues (block 148) until a reprogramming command is received (block 150). Operation of the pacer in this new "safe" mode advantageously alerts the physician (who is the only one who can effectuate a reprogramming change) as to the difficulties the pacer had in sensing P-waves, and the arrhythmias that were experienced by the patient. The physician may then determine an appropriate course of action, e.g., reprogram to a still different mode of operation (block 154), perform additional tests, or the like.

At the point in the process where the R-wave rate is tested (block 144), if it is determined that the R-wave rate is not greater than the prescribed threshold, then the heart is probably not experiencing an arrhythmia, and any desired mode of operation can be initiated by the pacemaker (block 152), such as a VVI or VVT mode. This mode continues (block 148) until a new reprogramming command is received (block 150).

As described above, the present invention thus provides a pacer which provides all the advantages of atrial rate based pacing, but which also avoids some of the problems associated with atrial rate based pacing in the event an atrial arrhythmia condition develops. More particularly, if the atrial rate exceeds a prescribed upper rate limit, $T_2$, then the pacer is switched automatically to a non atrial rate based mode.

Further, during this non-atrial rate based pacing mode, the rate of the pacer is controlled by a physiological sensor, such as an activity sensor. As soon as the atrial rate falls below another prescribed rate threshold, $T_3$, then the pacing mode automatically switches back to the initial atrial rate based mode. Moreover, the pacer includes means for automatically adjusting the sensitivity of the atrial channel in the event P-waves are not consistently sensed.

It should be noted that the automatic adjusting procedures described herein for adjusting the atrial channel may be used to adjust the atrial channel sensitivity in either direction, thereby allowing an optimum value of sensitivity to be automatically maintained.

Although an exemplary embodiment of the present invention has been shown and described, it will be apparent to those having ordinary skill in the art that a number of changes, modifications, or alterations to the invention as described herein may be made, none of which depart from the spirit or scope of the present invention. All such changes, modifications, and alterations should therefore be seen as within the scope of the present invention. Accordingly, the complete scope of the present invention should be determined with reference to the claims set forth below.

What is claimed is:

1. An improved dual chamber pacemaker having programmable modes of operation, said pacemaker being capable of stimulating the atrial and the ventricular chambers of the heart, said pacemaker including programming means for selectively allowing the pacemaker to be programmed to operate in an atrial rate based mode of operation, and atrial sensing means for sensing atrial activity occurring in the atrial chamber, including atrial rate of said atrial activity, wherein the improvement comprises:
   first sensing means for monitoring said atrial rate and sensing whether said atrial rate exceeds a first prescribed threshold;
   means for providing a stimulating pulse to a selected chamber of the heart at a maximum upper rate in the event said atrial rate sensed by said first sensing means exceeds said first prescribed threshold;
   second sensing means for monitoring said atrial rate above said first prescribed threshold and sensing whether said atrial rate exceeds a second prescribed threshold, said second threshold being at a higher rate than said first threshold; and
   means for automatically switching the mode of operation of said pacemaker from said atrial rate based mode of operation to a selected alternate mode of operation in the event said atrial rate exceeds said second prescribed threshold.

2. The programmable pacemaker of claim 1 further comprising:
   third sensing means for monitoring said atrial rate during said alternate mode of operation and sensing whether it drops below a third prescribed threshold; and
   means for automatically switching the mode of operation of said pacemaker from said alternate mode of operation back to said atrial rate based mode of operation in the event said atrial rate falls below said third prescribed threshold.

3. The programmable pacemaker of claim 2 wherein said first, second and third prescribed thresholds are programmably selectable through said programming means.

4. The programmable pacemaker of claim 2 wherein said first prescribed threshold comprises a rate which is at least equal to said maximum upper rate at which stimulating pulses are provided to the selected chamber of the heart.

5. The programmable pacemaker of claim 4 wherein said first prescribed threshold comprises a rate which is at least 150 beats per minute and said second prescribed threshold comprises a rate which is at least 200 beats per minute.

6. The programmable pacemaker of claim 1 further comprising:
   a physiological sensor coupled to said pacemaker, wherein said automatic switching means is capable of coupling said physiological sensor to said stimulating pulse providing means during said alternate mode of operation, and for modifying the operation of said pulse providing means to provide stimulating pulses to a selected chamber of the heart at a rate controlled by said physiological sensor during said alternate mode of operation.

7. The pacemaker of claim 1 further comprising:
   atrial sensitivity adjustment means for automatically checking the sensitivity of said atrial sensing means at selected intervals to determine its ability to sense P-waves, and for automatically adjusting said atrial sensing means to sense P-waves in the event that P-waves are not being sensed.

8. The pacemaker of claim 7 wherein said atrial sensitivity adjustment means comprises:

means for switching said pacemaker to a test mode of operation;

means for monitoring said atrial sensing means during said test mode for a prescribed period of time to determine if any P-waves are detected; and means for adjusting said atrial sensing means so that lower amplitude P-waves can be detected by said atrial sensing means in the event no P-waves are detected by said monitoring means during said prescribed period of time.

9. The pacemaker of claim 8 wherein said means for adjusting said atrial sensing means comprises:

means for adjusting the sensitivity of said atrial sensing means in a series of incremental adjustments until said P-waves are detected.

10. The pacemaker of claim 9 wherein said pacemaker further comprises:

means for switching the pacemaker mode of operation from said test mode to a prescribed alternate mode of operation in the event P-waves are not detected after the sensitivity of said atrial sensing means has been adjusted through all of said fixed incremental adjustments, whereby said alternate mode of operation provides an indicia that said atrial sensing means was unable to detect P-waves.

11. A dual chamber pacemaker having first and second channels, said first and second channels including sensing means for sensing cardiac activity and pulse generating means for providing pacing pulses in the absence of cardiac activity in the atrial and the ventricular chambers of the heart, respectively, said pacemaker comprising:

control means for controlling said sensing means and said pulse generating means of said first and second channels in a prescribed mode of operation, said control means comprising:

means for detecting a rate of cardiac activity as sensed by said sensing means in said first channel; and means for triggering said pulse generating means to provide pacing pulses in said second channel at a rate which is the lesser of said rate of cardiac activity detected in said first channel or a maximum tracking rate; and means for automatically changing said prescribed mode of operation in the event said rate of cardiac activity detected in said first channel exceeds a specified threshold level, said specified threshold level comprising a rate which is greater than said maximum tracking rate.

12. The pacemaker of claim 11 further comprising:

means for automatically changing the mode of operation of said pacemaker back to said prescribed mode of operation in the event said rate of cardiac activity detected in said first channel drops below a second specified threshold level, said second specified threshold level comprising a rate that is less than said maximum tracking rate.

13. The pacemaker of claim 11 further comprising:

means for automatically adjusting the ability of said first channel to sense cardiac activity.

14. The pacemaker of claim 11 further comprising:

a physiological sensor for sensing physiological events indicative of a need to change the rate of said pulse generating means, and wherein said means for automatically changing the prescribed mode of operation comprises means for coupling said physiological sensor to said pulse generating means and for controlling said pulse generating means to provide pulses in said second channel at a rate determined by the physiological events sensed by said physiological sensor.

15. A method of operating a dual chamber programmable pacemaker, said pacemaker being capable of operating in a variety of modes of operation and being initially programmed to operate in an atrial rate based mode of operation, said pacemaker comprising means for sensing cardiac activity in the atrial and the ventricular chambers of a heart, and means for selectively providing a stimulating pulse to either chamber of the heart at prescribed times and under prescribed conditions, the method comprising the steps of:

(a) sensing when the atrial rate exceeds a first rate threshold;

(b) providing a stimulating pulse to a selected chamber of the heart at a maximum upper rate in the event the atrial rate sensed in step (a) exceeds said first rate threshold;

(c) monitoring the atrial rate above said first rate threshold up to a second rate threshold; and (d) automatically switching the mode of operation of said pacemaker from said atrial rate based mode of operation to a selected alternate mode of operation in the event the atrial rate exceeds said second rate threshold.

16. The method of claim 15 further comprising the steps of:

(e) monitoring the atrial rate during said alternate mode of operation; and (f) automatically switching the mode of operation of said pacemaker from said alternate mode of operation back to said atrial rate based mode of operation in the event the atrial rate falls below a third rate threshold.

17. The method of claim 15 further comprising the step of:

(e) controlling the rate at which stimulating pulses are provided by said pacemaker during said alternate mode of operation in accordance with a rate signal provided by a physiological sensor coupled to said pacemaker.

18. The method of claim 15 further comprising the step of:

(e) checking the sensitivity of the atrial sensing means at selected intervals to determine its ability to sense P-waves; and (f) automatically adjusting the sensitivity of the atrial sensing means to sense P-waves in the event that P-waves are not being sensed.

19. The method of claim 18 wherein the step of checking the sensitivity of the atrial sensing means comprises:

monitoring the atrial sensing means for a prescribed period of time to determine if any P-waves are detected.

20. The method of claim 18 wherein the step of adjusting the sensitivity to sense P-waves comprises:

changing the sensitivity of the atrial sensing means by a first discrete increment;

checking the sensitivity of the atrial sensing means to determine if P-waves are sensed;

if P-waves are not sensed, changing the sensitivity of the atrial sensing means again by a second discrete increment, checking the sensitivity of the atrial sensing means again to determine if P-waves are sensed, and so on, through a series of discrete increments, until P-waves are sensed.

* * * * *

US004944298C1

(12) EX PARTE REEXAMINATION CERTIFICATE (6197th)
United States Patent
Sholder

(10) Number: US 4,944,298 C1
(45) Certificate Issued: Apr. 22, 2008

(54) ATRIAL RATE BASED PROGRAMMABLE PACEMAKER WITH AUTOMATIC MODE SWITCHING MEANS

(75) Inventor: Jason A. Sholder, Northridge, CA (US)

(73) Assignee: Pacesetter, Inc., Sylmar, CA (US)

Reexamination Request:
No. 90/006,642, May 19, 2003

Reexamination Certificate for:
Patent No.: 4,944,298
Issued: Jul. 31, 1990
Appl. No.: 07/355,588
Filed: May 23, 1989

(51) Int. Cl.
*A61N 1/00* (2006.01)

(52) U.S. Cl. .......................... 607/14; 607/30
(58) Field of Classification Search .............. 607/4, 607/9, 14, 17–26
See application file for complete search history.

(56) References Cited

U.S. PATENT DOCUMENTS

| | | | |
|---|---|---|---|
| 3,593,718 A | 7/1971 | Krasner et al. | 128/419 |
| 3,650,277 A | 3/1972 | Sjostrand et al. | 128/419 |
| 3,794,045 A | 2/1974 | Thaler | 128/419 |
| 4,009,721 A | 3/1977 | Alcidi | 128/419 |
| 4,049,003 A | 9/1977 | Walters et al. | 128/419 |
| 4,059,116 A | 11/1977 | Adams | 128/419 PG |
| 4,140,132 A | 2/1979 | Dahl | 128/419 |
| 4,169,480 A | 10/1979 | Digby et al. | 128/419 |
| 4,201,219 A | 5/1980 | Bozal Gonzalez | 128/419 |
| 4,237,897 A | 12/1980 | Beane et al. | 128/419 PG |
| 4,263,915 A | 4/1981 | McDonald et al. | 128/419 PG |
| 4,273,132 A | 6/1981 | Hartlaub et al. | 128/419 |
| 4,305,396 A | 12/1981 | Wittkampf et al. | 128/419 PG |
| 4,313,442 A | 2/1982 | Knudson et al. | 128/419 PG |
| 4,340,062 A | 7/1982 | Thompson et al. | 128/419 |
| 4,363,325 A | 12/1982 | Roline et al. | 128/419 PG |
| 4,365,633 A | 12/1982 | Loughman et al. | 128/419 |
| 4,388,927 A | 6/1983 | Schober | 128/419 PG |
| 4,390,020 A | 6/1983 | Herpers | 128/419 PG |
| 4,390,022 A | 6/1983 | Calfee et al. | 128/419 |
| 4,401,119 A | 8/1983 | Herpers | 128/419 |
| 4,404,972 A | 9/1983 | Gordon et al. | 128/419 |
| 4,412,541 A | 11/1983 | Schaldach et al. | 128/419 PG |
| 4,421,114 A | 12/1983 | Berkovits et al. | 128/419 PG |
| 4,428,378 A | 1/1984 | Anderson et al. | 128/419 PG |

(Continued)

FOREIGN PATENT DOCUMENTS

| | | |
|---|---|---|
| EP | 0 015 779 A1 | 9/1980 |
| EP | 0 056 745 A2 | 7/1982 |
| EP | 0 064 002 A2 | 11/1982 |

(Continued)

OTHER PUBLICATIONS

"Defendants' Third Supplemental Response and Amended Response to Plaintiff's First Set of Interrogatories (Nos. 1–10)," served Jun. 20, 2003 by defendants in *Pacesetter, Inc. v. Cardiac Pacemakers, Inc. et al*, Civ. No. 02–1337 (D. Minn.).

(Continued)

*Primary Examiner*—George R. Evanisko

(57) ABSTRACT

An atrial rate based programmable pacemaker including means for preventing the heart from being paced at an upper rate limit for prolonged periods of time is disclosed which paces the heart at a rate that follows or tracks the atrial rate up to the upper rate limit of the pacemaker, at which point the pacemaker stimulates the heart at the upper rate limit, but also continues to monitor the atrial rate. If the monitored atrial rate exceeds a second upper rate limit, a fast atrial arrhythmia or tachycardia condition is deemed to exist, and the pacemaker automatically switches from its existing mode of operation to an alternate mode of operation in an attempt to break or terminate the fast atrial condition. Alternate embodiments include using an external activity or physiological sensor to control the pacing rate in the new pacing mode, and the inclusion of means for periodically verifying that atrial sensing is occurring, and means for automatically adjusting the sensitivity of the atrial channel as required.

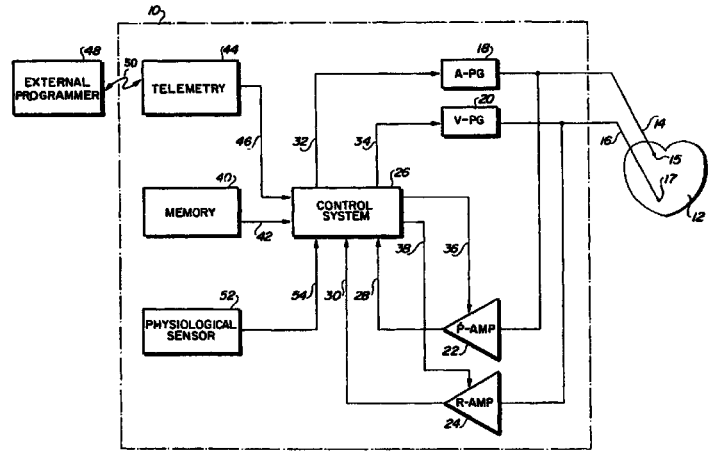

U.S. PATENT DOCUMENTS

| | | | |
|---|---|---|---|
| 4,429,697 A | 2/1984 | Nappholz et al. | 128/419 |
| 4,436,092 A | 3/1984 | Cook et al. | 128/419 |
| 4,467,807 A | 8/1984 | Bornzin | 128/419 PG |
| 4,467,810 A | 8/1984 | Vollmann | 128/419 PG |
| 4,485,818 A | 12/1984 | Leckrone et al. | 128/419 PG |
| 4,503,857 A | 3/1985 | Boute et al. | 128/419 |
| 4,527,568 A | 7/1985 | Rickards | 128/419 PG |
| 4,535,774 A | 8/1985 | Olson | 128/419 |
| 4,539,991 A | 9/1985 | Boute et al. | 128/419 |
| 4,543,954 A | 10/1985 | Cook et al. | 128/419 |
| 4,550,732 A | 11/1985 | Batty, Jr. et al. | 128/419 |
| 4,554,921 A | 11/1985 | Boute et al. | 128/419 PG |
| 4,562,841 A | 1/1986 | Brockway et al. | 128/419 PG |
| 4,567,892 A | 2/1986 | Plicchi et al. | 128/419 |
| 4,576,183 A | 3/1986 | Plicchi et al. | 128/723 |
| 4,596,251 A | 6/1986 | Plicchi et al. | 128/419 PG |
| 4,624,260 A | 11/1986 | Baker, Jr. et al. | 128/419 PG |
| 4,686,987 A | 8/1987 | Salo et al. | 128/419 PG |
| 4,688,573 A | 8/1987 | Alt | 128/419 PG |
| 4,708,144 A | 11/1987 | Hamilton et al. | 128/419 PG |
| 4,712,555 A | 12/1987 | Thornander et al. | 128/419 PG |
| 4,712,556 A | 12/1987 | Baker, Jr. | 128/419 PG |
| 4,714,079 A | 12/1987 | Hedberg et al. | 128/419 PG |
| 4,716,887 A | 1/1988 | Koning et al. | 128/419 |
| 4,719,920 A | 1/1988 | Alt et al. | 128/419 PG |
| 4,719,921 A | 1/1988 | Chirife | 128/419 PG |
| 4,722,341 A | 2/1988 | Hedberg et al. | 128/419 PG |
| 4,730,618 A | 3/1988 | Lekholm et al. | 128/419 |
| 4,776,338 A | 10/1988 | Lekholm et al. | 128/419 |
| 4,779,618 A | 10/1988 | Mund et al. | 128/419 |
| 4,788,980 A | 12/1988 | Mann et al. | 128/419 PG |
| 4,802,483 A | 2/1989 | Lindgren | 128/419 PG |
| 4,809,697 A | 3/1989 | Causey et al. | 128/419 |
| 4,830,006 A | 5/1989 | Haluska et al. | 128/419 PG |
| 4,856,523 A | 8/1989 | Sholder et al. | 128/419 PG |
| 4,860,751 A | 8/1989 | Callaghan | 128/419 |
| 4,870,968 A | 10/1989 | Wiertzfeld et al. | 128/419 |
| 4,890,617 A | 1/1990 | Markowitz et al. | 128/419 PG |
| 4,932,406 A | 6/1990 | Berkovits | 128/419 PG |
| 4,940,052 A | 7/1990 | Mann et al. | 128/419 PG |
| 4,944,298 A | 7/1990 | Sholder | 128/419 |
| 5,123,412 A | 6/1992 | Betzold | 128/419 |
| 5,123,419 A | 6/1992 | Platt et al. | 128/697 |
| 5,301,669 A | 4/1994 | Duncan | 607/9 |
| 5,388,586 A | 2/1995 | Lee et al. | 128/704 |
| 5,507,783 A | 4/1996 | Buchanan | 607/14 |
| 5,514,164 A | 5/1996 | Mann et al. | 607/25 |
| 5,522,857 A | 6/1996 | van Krieken | 607/9 |
| 5,788,717 A | 8/1998 | Mann et al. | 607/14 |

FOREIGN PATENT DOCUMENTS

| | | |
|---|---|---|
| EP | 0 077 844 A1 | 5/1983 |
| EP | 0 077 845 A1 | 5/1983 |
| EP | 0 089 014 A2 | 9/1983 |
| EP | 0 107 483 A1 | 5/1984 |
| EP | 0 114 679 A2 | 8/1984 |
| EP | 0 140 472 A1 | 5/1985 |
| EP | 0 147 820 B1 | 7/1985 |
| EP | 0 160 801 A2 | 11/1985 |
| EP | 0 201 990 A2 | 11/1986 |
| EP | 0 218 789 A1 | 4/1987 |
| EP | 0 426 828 B1 | 12/1997 |
| FR | 2 524 807 | 10/1983 |
| GB | 2 153084 A | 8/1985 |
| WO | WO 81/01659 | 6/1981 |

OTHER PUBLICATIONS

Amundson et al., "A P–Wave Controlled, Rate Responsive Pacer Algorithm," PACE, vol. 4, Abstract, May–Jun. 1981: A–81.

Berkovits et al., "Improved DDD Pacing with a New Rate–Limiting Algorithm," Proceedings of the VIIIth World Symposium on Cardiac Pacing and Electrophysiology, 1986 (or later): 171–176.

Delta Model 925 (Type DDD, Dual Chamber Pulse Generator) Physician's Manual (Cardiac Pacemakers, Inc.).

Donaldson et al., "Towards Multisensor Pacing," American Heart Journal, vol. 106, No. 6, Dec. 1983: 1454–1457.

French et al., "Physiological Benefits of a Pacemaker with Dual Chamber Pacing at Low Heart Rates and Single Chamber Rate Responsive Pacing During Exercise," Pace, vol. 11, Nov. 1988, Part II: 1840–1845.

Furman, "Dual Chamber Pacemakers: Upper Rate Behavior," Pace, vol. 8, Mar.–Apr. 1985: 197–214.

Jacobson et al., "Advantages and Disadvantages of Various Upper and Lower Rate Responses," Pace, vol. 7, Nov.–Dec. 1984, Part II: 1183–1186.

Knudson et al., "Hemodynamic Demands—Are They Met By a Rate Responsive Physiologic Pacemaker?," Pace, vol. 4, Abstract, May–Jun. 1981: A–53.

Knudson et al., "Hemodynamic Demand Pacing," The Third Decade of Cardiac Pacing, Part II, Chapter Four, 1982: 249–264.

Kruse et al., "Clinical Evaluation of Atrial Synchronous Venticular Inhibited Pacemakers," Pace, vol. 3, Nov.–Dec. 1980: 641–650.

Leckrone et al., "A Microprocessor–Based, Two–Chamber Physiologic Pacemaker," The Third Decade of Cardiac Pacing, Part II, Chapter One, 1982: 167–189.

Levine et al., "Analysis of AV Universal (DDD) Pacemaker Rhythms," Clin. Prog. Pacing and Electrophysiol., vol. 2, No. 1, 1984: 54–70.

Pehrsson et al., "A New Concept for Atrial Triggered Pulse Generators," Pace, vol. 2, Nov.–Dec. 1979: 560–567.

"Defendants' Response to Plaintiff's First Set of Interrogatories (Nos. 1–10)," served Jun. 21, 2002 by defendants in *Pacesetter, Inc. v. Cardiac Pacemakers, Inc. et al.* Civ. No. 02–1337 (D. Minn.).

"Defendants' Supplemental Response to Plaintiff's First Set of Interrogatories (Nos. 1–10)," served Feb. 6, 2003 by defendants in *Pacesetter, Inc. v. Cardiac Pacemakers, Inc. et al.* Civ. No. 02–1337 (D. Minn.).

"Defendants' Second Supplemental Response to Plaintiff's First Set of Interrogatories (Nos. 1–10)," served May 2, 2003 by defendants in *Pacesetter, Inc. v. Cardiac Pacemakers, Inc. et al.* Civ. No. 02–1337 (D. Minn.).

European Patent Office, "Communication pursuant to Article 96(2) and Rule 51(2) EPC" re Application No. EP–90908802.3 (EP–0 426 828) (Nov. 12, 1993).

European Patent Office, "Communication pursuant to Article 96(2) and Rule 51(2) EPC" re Application No. EP–90908802.3 (EP–0 426 828) (Sep. 8, 1994).

European Patent Office, "Communication pursuant to Article 96(2) and Rule 51(2) EPC" re Application No. EP–90908802.3 (EP–0 426 828) (Nov. 13, 1995).

European Patent Office, "Communication pursuant to Article 96(2) and Rule 51(2) EPC" re Application No. EP–90908802.3 (EP–0 426 828) (Mar. 6, 1996).

"Advances In Dual–Chamber Pacing" (Intermedics Inc), Medical Electronics, No. 88, pp. 183–190 (Apr. 1986).

Advertisement for Diplos 04 Pacer from Biotronik; Pace, vol. 17, No. 3, Part I (May 1984).

Advertisement for Cosmos Pacing System from Intermedics, Inc.; Pace, vol. 17, No. 3, Part I (May 1984).

E. Alt, R. Volker, and A. Wirtzfeld, "Directly and Indirectly Measured Respiratory Parameters Compared with Oxygen Uptake and Heart Rate," Pace, vol. 8, Part II, No. 3, p. A–21 (May/Jun. 1985).

E. Alt, C. Hirgstetter, M. Heinz, "Central Venous Blood Temperature (CPT) for Control of Pacemaker (PM) Rate," Pace, Vo. 8, No. 3, Part II, p. A–78 (May 1985).

E. Alt, A. Wirtzfeld, "Physiological Pacing and Biological Rate Adjustment," Cardiac Pacemakers, pp. 87–99 (1985).

E. Alt, H. von Bibra, and H. Blomer, "Different Beneficial AV Intervals With DDD Pacing After Sensed Or Paced Atrial Events," Journal of Electrophysiology, vol. 1, No. 3, pp. 250–256 (1987).

R. Cowell, J. Morris–Thurgood, V. Paul, and C. Ilsley, "A Gold Standard for the Programming of Rate Adaptive Pacemakers: the Renaissance of the Sinus Mode," Cardio Stimolazione, vol. 10, No. 3, p. 235 (Dec. 1992).

A. Le Helloco, B. Lelong, M. Bedossa, V. Pasquali, M. Laurent, C. Almange, "Clinical Experience of an Acceleration Responsive Dual Chamber: Intermedics Relay Model 194–03," Cardio Stimolazione, vol. 10, No. 3, p. 240 (Dec. 1992).

E. Alt, "A Protocol for Treadmill and Bicycle Stress Testing Designed for Pacemaker Patients," Stimucoeur, vol. 15, No. 1, pp. 33–35 (1987).

J.Alzueta, I.Alvarez, C.Escudero, J.Moreu, A.Puente, J.L.Castillo–Olivares, and J. Marquez–Montes, "Bradycardia in an Experimental Model of Denervated Heart An Unusual Finding," Pace, vol. 10, Part II, p. 633 (May/Jun. 1987).

G. Amitzur, S. Rogel, and S. Samueloff, "The Modulating Effect of Thyroid Hormones on Ventricular Fibrillation Threshold in the Dog," Pace, vol. 10, Part II, p. 633 (May/Jun. 1987).

D.C. Amundson, M.B. Knudson, T.R. Hudrlik, D.J. MacCarter, A.W. Thornton, "A P–Wave Controlled Rate Responsive Algorithm," Cardiac Pacing, pp. 1239–1243 (1982).

K. Anderson, D. Humen, G. J. Klein, D. Brumwell, S. Huntley, "A Rate Variable Pacemaker Which Automatically Adjusts For Physical Activity," Pace, vol. 6, p. A–12, VIIth World Symposium (May 1983).

G.E. Antonioli, G. Boriani, N. Bottoni, A. Capucci, G. Guardigli, M. Marconi, C. Menozzi, S. Sermasi, S. Silvani, T. Toselli, and G. Tumiotto, "Multicenter Study of Evaluation on DDDR vs DDD Pacing," Cardio Stimolazione, vol. 10, No. 3, p. 238 (Dec. 1992).

S.S. Barold, M.D. Falkoff, L. S. Ong, R. A. Heinle, "Characterization of Pacemaker Arrhythmias Due to Normally Functioning AV Demand (DVI) Pulse Generators," Pace, vol. 3, pp. 712–723 (Nov./Dec. 1980).

S.S. Barold, M.D. Falkoff, L.S. Ong, R.A. Heinle, "Interpretation Of Electrocardiograms Produced by a New Unipolar Multiprogrammable 'Committed' AV Sequential Demand (DVI) Pulse Generator," PACE, vol. 4, pp. 692–708 (Nov./Dec. 1981).

S.S. Barold, L.S. Ong,, M.D. Falkoff, R.A. Heinle, "Programmable Pacemakers—Clinical Indications, Compilations and Future Directions," The Third Decade of Cardiac Pacing, pp. 27–76 (1982).

S.S. Barold, M.D. Falkoff, L.S. Ong, R.A. Heinle, "Oversensing by Single–Chamber Pacemakers: Mechanisms, Diagnosis, and Treatment," Cardiology Clinics, pp. 565–585 (Nov. 1985).

S.S. Barold, P.H. Belott, "Behavior of the Ventricular Triggering Period of DDD Pacemakers," Pace, vol. 10, pp. 1237–1252 (Nov./Dec. 1987).

S.S. Barold, M.D. Falkoff, L.S. Ong, R.A. Heinle, "Upper Rate Response of DDD Pacemakers," New Perspectives in Cardiac Pacing, pp. 121–172 (1988).

R.L. Batey, D.A. Calabria, S. Shewmaker, M. Sweesy, "Crosstalk and Blanking Periods In a Dual Chamber (DDD) Pacemaker: A Case Report," Clin. Prog. Electrophysiol. and Pacing, vol. 3, No. 4, pp. 314–318 (1985).

D.G. Benditt, D. Dunbar, D. Woodrow Benson, Jr., A. Dunningan, A. Almquist, M. Mianulli, J. Fetter, "Improved Exercise Capacity with a Rate–Responsive Pacemaker which Detects and Tracks Physical Activity," Abstracts of the 58th Scientific Sessions, p. III–433 (Nov. 1985).

T. Bennett, "Dynamic Characteristics of Alternative Physiological Pacing Modes"—Abstract, Pace, vol. 8, No. 2, p. 294 (Mar./Apr. 1985).

T.D. Bennett, W.H. Olson, G.A. Bornzin, M.D. Baudino, "Alternative Modes for Physiological Pacing," Pace, vol. 8, Part II, p. A–69 (May/Jun. 1985).

N.D. Berman, S.E. Dickson, B.M. Walker, I.H. Lipton, "Documenting the Value of Rate Hysteresis," Cardiac Pacing, pp. 597–599 (1982).

C. Bernheim, A. Markewitz, and R.M. Kemkes, "Can Reprogramming of Atrial Sensitivity Avoid an Endless Loop Tachycardia?" Pace, vol. 9, p. 293 (Mar./Apr. 1986).

M. Bilitch, R.S. Cosby, E.A. Caffery, "Ventricular Fibrillation and Competitive Pacing," New England Journal of Medicine, vol. 276, No. 11, pp. 598–903 (Mar. 1967).

G. Boriani, A. Capucci, S. Specchia, M. Marinelli, A. Santarelli, M. Biffi, B. Magnani, "DDR Versus DDD Pacing: A Comparison by Means of Cardiopulmonary Exercise Test," Cardio Stimolazione, vol. 10, No. 3, p. 240 (Sep. 1992).

T. Bunge, D. Thompson, "Sensing Internal and External Body Activities," Pace, vol. 8, p. A–110, pp. 786–791 (May/Jun. 1985, Part II).

C.L. Byrd, S.J. Schwartz, M. Gonzales, R.J. Ciraldo, W.Z. Yahr, M. Sivina, and J.J. Greenberg, "Rate Responsive Pacemakers and Cross Talk"—Abstract, Pace, vol. 11, p. 798 (Jun. Supplement 1988).

R.V. Calfee, P. Gordon, R.G. Baker, "Technical Advances in Cardiac Pacing—An Engineering Point of View," The Third Decade of Cardiac Pacing, pp. 471–477 (1982).

R. V. Calfee, "Dual–Chamber Committed Mode Pacing," Pace, vol. 6, pp. 367–391 (Mar./Apr. 1983, Part II).

L. Cammilli, L. Alcidi, G. Papeschi, "A New Pacemaker Autoregulating the Rate of Pacing In Relation to Metabolic Needs," Cardiac Pacing, pp. 414–419 (1977).

L. Cammilli, "The Autoregulating Pacemaker," Cardiac Pacing, pp. 1261–1262 (1982).

L. Cammilli, L. Alcidi, E. Shapland, S. Obino, "Results, Problems and Perspectives with the Autoregulating Pacemaker," Pace, vol. 6, pp. 488–493 (Mar./Apr. 1983, Part II).

A. Castellanos, B.V. Berkovits, R. Fox, "QRS–Trigrered Pacemaker and Arrhythmias Related to Early Systolic Stimulation," Annals of Cardiology, No. 4, pp. 485–490 (1971).

K. Chadda, B. Bloomfield, D. Harrington, R. Arbouet, J. Neglia, M. Bondenheimer, B. Berkovits, "Interruption of Spontaneous and Induced Tachyarrhythmias by Scanning Self–Adapting Overdrive Pacing," Journal of the American College of Cardiology, vol. 9, No. 2, Supplement A, p. 141A (Feb. 1987).

W. M. Chardack, H. Ishikawa, F.J. Fochler, S. Souther, A.A. Gage, "Pacing and Ventricular Fibrillation," Annals New York Academy of Sciences, pp. 919–933 (1969).

G. Charos, C. Haffajee, B. Berkvits, R. Gold, A. Castellanos, J.S. Alpert, "An Effective and Potentially Superior Mode of Overdrive Pacing for Ventricular Tachycardia Interruption," Pace, vol. 8, p. 294; (Mar./Apr. 1985).

R.D. Fletcher, A. Cohen, A. Del Negro, M. Gomes, D.J. Cutler, S. Singh, R. DiBianco, "Patient Programming of Standard Implanted Pacemakers to Terminate Tachyarrhythmias," VIIth World Symposium, PACE, vol. 6, No. 3, Part II, p. A–138 (May 1983).

T. Cohen, "A Theoretical Right Atrial Pressure Feedback Heart Rate Control System to Restore Physiologic Control to the Rate–Limited Heart," PACE, vol. 7, pp. 671–677 (Jul./Aug. 1984).

W.J. Combs, D.W. Reynolds, A.D. Sharma, T.D. Bennett, "Cross–Talk in Bipolar Pacemakers," Pace, vol. 12, pp. 1613–1621 (Oct. 1989).

J.R. Cook, "Pacing Systems in The 80s," J. Louisiana State Medical Society, vol. 137, No. 4, pp. 40–50 (Apr. 1985).

M.J.E. Davis, G.C. Mews, G.D. Cope, "Initial Experience with Physiological Pacing," Aust. NZ. J. Med., vol. 15, pp. 246–251 (1985).

M. Davis, M. Pitney, C. May, "Automatic Mode Switching and Program Selection in a Rate Adaptive Dual Chamber Pacemaker," Pace, vol. 14, p. 664 (Apr. 1991, Part II).

O. de Divitiis, M. Santomauro, S. Fazio, M. Petitto, V. Liguori, B. Villari, C. Iaconon, S. Ferraro, M. Salvatore, "Cardiac Function in Patients with Breathing Frequency Controlled Pacemaker," Pace, vol. 8, p. A–9 (May/Jun. 1985, Part II).

K. den Dulk, D. Richards, H.J.J. Wellens, M. Bertholet, J.C. Demoulin, A. Waleffe, H.E. Kulbertus, F.W. Lindemans, "A Versatile Pacemaker System with a Programmable Patient Activator for Termination of Tachycardias," Pace, vol. 6, No. 3, Part II, p. 508 (May 1983).

B.G. Denys, A.E. Aubert, H. Ector, and H. De Geest, "Intramyocardial Pressure at Various Pacing Rates," Pace, vol. 8, p. A–69 (May/Jun. 1985, Part II).

V. DiCola, J. Hawthorne, "Physiological Pacemakers," American Review of Medicine, vol. 35, 493–502 (1984).

R.M. Donaldson, K. Fox, A.F. Rickards, "Initial Experience with A Physiological, Rate Responsive Pacemaker," British Medical Journal, vol. 286, pp. 667–671 (Feb. 1983).

R.M. Donaldson, A.F. Rickards, "A Microprocessor Based Algorithm Controlled Antiarrhythmic and Rate–Responsive Pacemaker," Computers in Cardiology, 10th Annual Meeting, pp. 353–355 (Oct. 1983).

R.M. Donaldson, A.F. Rickards, "Rate Responsive Pacing Using the Evoked QT Principle. A Physiological Alternative to Atrial Synchronous Pacemakers," Pace, vol. 6, pp. 1344–1349 (Nov./Dec. 1983).

R.M. Donaldson, A.F. Rickards, "Towards Multisensor Pacing," American Heart Journal, vol. 106, No. 6, pp. 1454–1457 (Dec. 1983).

D. Escher, "Pacemakers of The 1980's," Medical Instrumentation, vol. 18, No. 1, pp. 29–34 (Jan./Feb. 1984).

S. Faerestrand, O.J. Ohm, "A Longitudinal Study of the Hemodynamic Benefit of Atrio–Ventricular Snychronous Pacing Evaluated by Doppler Echocardiography," Pace, vol. 8, p. A–9, (May/Jun. 1985, Part II).

L. Fananapazir, M. Rademaker, D. Bennett, "Performance of the TX Pacemaker," Pace 8, p. A–110 (May/Jun. 1985, Part II).

L. Fananapazir, M. Rademaker, D.H. Bennett, "Reliability of the Evoked Response In Determining the Paced Ventricular Rate and Performance of the QT or Rate Responsive (TX) Pacemake," Pace, vol. 8, pp. 701–714 (Sep./Oct. 1985).

N.E. Fearnot, L.A. Geddes, H.J. Smith, "Principles of Exercise Responsive Pacemakers," Engineering In Medicine & Biology, pp. 25–29 (Jun. 1984).

N. Fearnot, D. Jolgren, W. Tacker, L. Geddes, "Exercise Responsive Pacing Using RV Blood Temperature," 37th Acemb, p. 216 (Sep. 1984).

N.E. Fearnot, D.L. Jolgren, W.A. Tacker, J.P. Nelson, L.A. Geddes, "Increasing Cardiac Rate by Measurement of Right Ventricular Temperature," PACE, vol. 7, pp. 1240–1245 (Nov./Dec. 1984, Part II).

N.E. Fearnot, D.L. Jolgren, T.D. Sellers, "Pacemakers Update: Temperature," Research Digest Condensed Version, vol. 1, No. 1; pp. 1–9 (1985).

G.A. Feruglio, A.F. Rickards, K. Steinbach, B.S. Goldman, V. Parsonnet, A. Dussault, "Pacing in the World Today," VIIth World Symposium, Pace, vol. 6, p. A–149 (May 1983).

J.D. Fisher, G. Katz, S. Furman, I. Rubin, "Differential Response to Carotid Sinus Massage in Cardiac Patients With and Without Syncope," Pace, vol. 4, p. A–11 (May/Jun. 1981).

J.D. Fisher, S.G. Kim, E. Ostrow, "Ultra–Rapid Single Capture Train Stimulation for Termination of Ventricular Tachycardia," Pace, vol. 4, p. A–11 (May/Jun. 1981).

R.D. Fletcher, A. Cohen, R. Cohen, A. Del Negro, D.J. Cutler, J.G. Keimel, "Serial Noninvasive Electrophysiologic Testing Using Implanted Single And Dual Chamber Pacemakers," VIIth World Symposium Pace, vol. 6, No. 3, Part II, p. 563 (May 1983).

R.D. Fletcher, J. Keimel, L. Larca, J. Cox, A. Del Negro, R. Di Bianco, S. Singh, "Non–invasive Serial Electrophysiologic Testing Using an Implanted Pacemaker to Track Chest Wall Stimuli," The American Journal of Cardiology, vol. 47, p. 392 (Feb. 1981).

R.D. Fletcher, A.I. Cohen, A. Del Negro, "Noninvasive Electrophysiologic Studies Using Implanted Pacemakers," Modern Cardiac Pacing, pp. 421–438 (May/Jun. 1985).

R.D. Fletcher, J.G. Keimel, L. Larca, J.A. Cox, A. Del Negro, R. Di Bianco, S. Singh, "Noninvasive Serial Electrophysiologic Testing Using an Implanted Pacemaker," Pace, vol. 4, p. A–11 (May–Jun. 1981).

R. Fletcher, J. Keimel, A. Cohen, R. Cohen, A. Del Negro, D.J. Cutler, "Synchronized Programming—A New Technique for Serial Noninvasive Electrophysiological Testing in Single and Dual Chamber Implanted Pacemakers," J. Am. Coll. Cardiol., vol. I, No. 2, p. 720 (1983).

R. Fletcher, A. Cohen, R. Cohen, B. Lee, D.J. Cutler, A. Del Negro, S. Singh, R. DiBianco; "Efficacy Of Noninvasive Electrophysiological Testing In Patients with Implanted Pacemakers To Control Arrhythmia," J. Am. Cardiol., vol. 3, No. 2, p. 538 (Feb. 1984).

R.D. Fletcher, A.I. Cohen, D. Joshua, A.A. Del Negro, B.I. Lee, J.S. Gottdiener, S.N. Singh, "Dual Chamber Pacemakers as Implanted Electrophysiology Laboratories," Circulation, vol. 70, No. 4, p. II–201 (Oct. 1984).

R. Flink, "Future Directions of Cardiac Pacemaker Research—A Survey," Medical Instrumentation, vol. 18, No. 1, pp. 25–28 (Feb. 1984).

G. Fontaine, R. Frank, J.C. Petitot, J. Vedel, F. Fillette, R. Dzietham, Y. Grosgogeat, "The Risks of Programmability," The Third Decade of Cardiac Pacing, pp. 77–103 (1982).

J. A. Franciosa, C.L. Leddy, M. Wilen. D.E. Schwartz, "Relation Between Hemodynamic and Ventilatory Responses in Determining Exercise Capacity In Severe Congestive Heart Failure," Am. J. Cardiol., vol. 53, pp. 127–134 (1984).

W.J. French; J.J. Florio, "Mode Change During DDD/Rate Responsive Pacing: Technical Benefits & Physiologic Results," Pace, vol. 11, p. 798 (Jun. Supplement 1988).

W.J. French, R.J. Haskell, G.W. Wesley, J. Florio, "Physiological Benefits of a Pacemaker with Dual Chamber Pacing at Low Heart Rates and Single Chamber Rate Responsive Pacing During Exercise," Pace, vol. 11, pp. 1840–1845 (Nov. 1988, Part II).

H.D. Friedberg, S.S. Barold, "On Hysteresis In Pacing," J. Electrocardiology, vol. 6, No. 1, pp. 1–2 (1973).

H.D. Funke, "Ein Herschrittmacher Mit Belastungsabhangiger Frequenzregulation (A Cardiac Pacemaker With Activity–Dependent Frequency Regulation)," Biomedizinische Technik, vol. 20, No. 6, pp. 225–228 (1975).

H.D. Funke, "Cardiac Pacing with Universal DDD Pulse Generator: Technology and Electrophysiological Considerations," The Third Decade of Cardiac Pacing, pp. 191–223 (1982).

S. Furman, H. Reicher–Reiss, D.J.W. Escher, "Atrioventricular Sequential Pacing and Pacemakers," Chest, vol. 63, No. 5, pp. 783–789 (May 1973).

S. Furman, "Dual Chamber Pacemakers: Upper Rate Behavior," Pace, vol. 8, pp. 197–214 (Mar./Apr. 1985).

S. Furman, "Pacemaker Sensing," Pace, vol. 9, p. 157 (Mar./Apr. 1996).

S. Furman, "Basic Concepts," A Practice of Cardiac Pacing, p. 27–73 (1986).

S. Furman, "Comprehension of Pacemaker Timing Cycles," A Practice of Cardiac Pacing, pp. 159–217 (1986).

M.D. Gabry, P. Klementowicz, S. Furman, "Balanced Endless Loop Tachycardia," Pace, vol. 9, (Mar./Apr. 1986).

D. Gascon, F. Errazquin, J. Nieto, J. Burgos, A. Diaz, B. Candelon, L. Castillion, "Preliminary Clinical Evaluation of a New DDDM Pacemaker (Quintech DDD931)," Pace, vol. 8, Part II, p. A–78 (May/Jun. 1985).

L.A. Geddes, N.E. Fearnot, H.J. Smith, "The Exercise–Responsive Cardiac Pacemaker," IEEE Transactions on Biomedical Engineering, vol. BME–31, No. 12, pp. 763–770 (Dec. 1984).

P. Gillette, "Critical Analysis of Sensors for Physiological Responsive Pacing," Pace, vol. 7, pp. 1263–1266, (Nov./Dec. 1984, Part II).

A. Goicolea de Oro, M.W. Ayza, R. de la Llana, J.A. Morales, J.R. Gutierrez Diez, J. Gonzalez Alvarez, "Rate–Responsive Pacing: Clinical Experience," Pace, vol. 8, p. 322–28 (May/Jun. 1985, Part I).

J.C. Griffin, A.P. Nielsen, W.L. Finke, J.W. Clark, "A New Method of Rhythm Identification: Endocardial Electrogram Morphology," Circulation, Part II, vol. 70, No. 4, p. 201 (Oct. 1984).

R. Haberl, E. Hengstenberg, G. Steinback, "Single Beat Analysis of Frequency Content in the Surface ECG for Identification of Patients with Ventricular Tachycardia," Abstracts of the 58th Scientific Sessions, p. III–433 (Nov. 1985).

C.I. Haffajee, J.C. Love, J.S. Alpert, "Is Pacemaker Mediated Tachycardia with DDD Pacemakers Obsolete? Follow–up Study on 81 Patients," Pace, vol. 7, p. 470 (May/Jun. 1984, Part I).

J.W. Harthorne, "The Future of Cardiac Pacing," Modern Cardiac Pacing, Ch. 43, pp. 949–958 (1985).

R.J. Haskell, W.J. French, "Rate Responsiveness or Atrial Augmentation as Most Important Physiological Factor in Enhanced Exercise Performance in Patients with Dual Chamber Pacemakers," JACC, vol. 9, No. 2, p. 141A (Feb. 1987).

R.G. Hauser, "The Electrocardiography of AV Universal DDD Pacemakers," Pace, vol. 6, pp. 399–409 (Mar./Apr. 1983, Part II).

R.G. Hauser, "Techniques for Improving Cardiac Performance with Implantable Devices," Pace, vol. 7, pp. 1234–1239 (Nov/Dec. 1984, Part II).

D.L. Hayes, "Pacemaker Electrocardiography," A Practice of Cardiac Pacing, pp. 305–331 (1986).

D.L. Hayes, S.T. Higano, G. Eisinger, "Utility of Rate Histograms in Programming and Follow–Up of a DDDR Pacemaker," Mayo Clin. Proc. vol. 64, pp. 495–502 (May 1989).

J.M. Herre, J.C. Griffin, T.D. Schuenemeyer, J.C. Luck, D.E. Mann, S. Magro, G.W. Lawrie, A.P. Nielsen, C.R.C. Wyndham, "Diagnostic and Therapeutic Use of Permanent Triggered Pacemakers in Ventricular Tachycardia," VIIth World Symposium, Pace, vol. 6, No. 3, Part II, p. A–138 (May 1983).

G. Hindricks, W. Haverkamp, L. Dreismann, J. Vogt, H. Gulker; "Electrophysiological and Antiarrythmic Efficacy of the New Propafenon–Derivative Hydroxyfenone," Pace, vol. 10, Part II, p. 688 (May/Jun. 1987).

L.K. Holley, D.L. Ross, K.J. Palmer, B. Ho, A.R. Dennis, J.B. Uther, "Analysis of Pacing Modalities for Ventricular Tachycardia Termination,", Pace, vol. 8, p. 294 (Mar./Apr. 1985).

W.J. Hollins, R.B. Leman, J.M. Kratz, P.C. Gillette, "Limitations of the Long–Term Clinical Application of Rate Hysteresis," Pace, vol. 10, pp. 302–304 (Mar./Apr. 1987).

D.R. Holmes, "Pacing for Tachycardia," A Practice of Cardiac Pacing, pp. 413–431 (1986).

J. Horgan, "Medical Electronics," IEEE Spectrum, pp. 89–94 (Jan. 1985).

E. Horstmann, "Brief Exercise and Double Sensor Pacing Based on QT Interval and Activity. Early Results with the Topaz," Cardio Stimolazione, vol. 10, No. 3, p. 239 (Sep. 1992).

D.P. Humen, K. Anderson, D. Brumwell, S. Huntley, G.J. Klein, "A Pacemaker which Automatically Increases its Rate with Physical Activity," Cardiac Pacing, pp. 259–264 (May 1983).

D. Humen, W.J. Kostuk, G.J. Klein, "Activity–Sensed, Rate Responsive Pacing: Treadmill Performance and Hemodynamic Characteristics," JACC, vol. 3, No. 2, p. 508 (Feb. 1984).

D.P. Humen, W.J. Kostuk, G.J. Klein, "Activity–Sensing, Rate–Responsive Pacing: Improvement in Myocardial Performance with Exercise," Pace, vol. 8, pp. 52–59 (Jan./Feb. 1985).

W. Imich, Letter to the Editor Re: Definition of Negative and Positive Hysteresis, Pace, vol. 5, pp. 283–285 (Mar./Apr. 1982).

W. Imich, "Interference in Pacemakers," Pace, vol. 7, pp. 1021–1048 (Nov./Dec. 1984, Part I).

D.L. Janosik, A.C. Pearson, T.A. Buckingham, A.J. Labovitz, R.M. Redd, D. Mrosek, "The Hemodynamic Benefit of Differential Atrioventricular Delay Intervals for Sensed and Paced Atrial Events During Physiologic Pacing," JACC, vol. 14, No. 2, pp. 499–507 (Aug. 1989).

D. Jolgren, N. Fearnot, L. Geddes; A Rate–Responsive Pacemaker Controlled by Right Ventricular Blood Temperature; Pace, vol. 7, pp. 794–801 (Sep./Oct. 1984, Part V).

B.A. Jones, R.E. Patterson, S.E. Epstein, "Electrical Instability as a Function of Myocardial Infarction Size," The American Journal of Cardiology, vol. 47, p. 392 (Feb. 1981).

W. Jung, M. Manz, B. Lüderitz, "Welche Programmierbaren Lesitungen Der Aggregate sind Verfügbar, und wie ist ihre Klinische Relevanz?" Herz, vol. 16, No. 3, pp. 158–170 (Jun. 1991).

I. Karlöf, "Haemodynamic Effect of Atrial Triggered versus Fixed Rate Pacing at Rest and During Exercise in Complete Heart Block," Acta Med. Scand., vol. 197, pp. 195–206 (1975).

R.A. Kenny, A. Ingram, T. Mitsuoka, K. Walsh, R. Sutton, "Comparison of Sensor Driven Physiological Pacing Systems," Pace, vol. 8, No. 5, p. 781 (Sep./Oct. 1985).

I.E. Kersschot, P. Ortmanns, M.A. Goethals, "Atrial Pacing Bigeminy: A Manifestation of Crosstalk," Pace, vol. 8, pp. 402–407 (May/Jun. 1985, Part I).

P.J. Kertes, C.J. Hilton, E.J. Jones, P.F. Walter, R.W.F. Campbell, "Surgical Management of Early Post–Infarction, Drug Resistant Ventricular Tachyarrhythmias," Pace, vol. 8, p. 781 (Sep./Oct. 1985).

P.J. Kertes, S.J. Pollack, P.F. Walter, "Programmed Stimulation for Ventricular Tachycardia: Responses Predicted by Signal Averaging in Patients with and without Coronary Disease," Abstracts of the 58$^{th}$ Scientific Sessions, p. III–433 (Nov. 1985).

F. Klementowicz, R. Steingart, S. Furman, "Atrial Contribution to Left Ventricular Volume Assessed by Ventriculography," Pace, vol. 8, p. A–9 (May/Jun. 1985, Part II).

M.B. Knudson, D. Amundson, A. Thornton, J. Shapland, M. Mosharrafa, "Hemodynamic Demands—Are They Met By A Rate Responsive Physiologic Pacemaker?" Pace, vol. 4, p. A–53 (May–Jun. 1981).

M.B. Knudson, D.C. Amundson, M. Mosharrafa, "Hemodynamic Demand Pacing," The Third Decade of Cardiac Pacing, pp. 249–264 (1982).

W.H. Ko, "A Review of Implantable Sensors," Pace, vol. 6, pp. 482–487 (Mar./Apr. 1983).

Y. Koretsune, K. Kodama, M. Inoue, S. Nanto, K. Taniura, M. Hori, M. Mishima, H. Abe, "Disadvantageous Effects of Ventricular Pacing on Cardiac Function and Myocardial Energetics," JACC, vol. 3, No. 2, p. 507 (Feb. 1984).

B.E. Kristensson, K. Arnman, P. Smedgard, L. Ryden, "Physiological Versus Single–Rate Ventricular Pacing: A Double–Blind Cross–Over Study," Pace, vol. 8, pp. 73–84 (Jan./Feb. 1985).

K. Kubisch, W. Peters, I. Chiladakis, H. Greve, H. Heuer, "Clinical Experience with the Rate Responsive Pacemaker Sensolog 703," Pace, vol. 11, pp. 1829–1833 (Nov. 1988, Part II).

A. Laczkovics, M. Schilck, U. Losert, G. Simbrunner, "The Use of Central Venous Blood Temeperature (CVT) as a Guide for Rate Control in Pacemaker–Therapy," VIIth World Symposium, Pace, vol. 6, p. A–12 (May 1983).

M.S. Lampadius; Event–Triggered Rheographic Ventilation Sensor for Pacemaker Rate Control; Pace, vol. 8, Part II, A–78 (May/Jun. 1985).

C.P. Lau, W.S. Tse, A.J. Camm, "Clinical Experience with Sensolog 703: A New Activity Sensing Rate Responsive Pacemaker," Pace, vol. 11, pp. 1444–1455 (Oct. 1988).

M.E. Leckrone, V.T. Cutolo, D. Ennen, E. Zayas, P. P. Tarjan, "A Microprocessor–Based, Two–Chamber Physiologic Pacemaker," The Third Decade of Cardiac Pacing— Advances in Technology and Clinical Applications, pp. 167–189 (1982).

L. Lemberg, A. Castellanos, A.G. Arcebal, B.V. Berkovits, O. Hernandez–Pierretti, "Systolic and Diastolic Pacemaker Induced Repetitive Firing in the Human Heart," Journal of Electrocardiology, pp. 353–362 (1969).

P.A. Levine, "Normal and Abnormal Rhythms Associated with Dual–Chamber Pacemakers," Cardiology Clinic, vol. 3, No. 4, pp. 595–616 (Nov. 1985).

P.A. Levine, B.S. Lindenberg, "Upper Rate Limit Circuit–Induced Rate Slowing," Pace, vol. 10, pp. 310–314 (Mar./Apr. 1987).

P.A. Levine, F.J. Venditti, P.J. Podrid, M.D. Klein, "Therapeutic and Diagnostic Benefits of Intentional Crosstalk Mediated Ventricular Output Inhibition," Pace, vol. 11, pp. 1194–1201 (Aug. 1988).

P.A. Levine, R.C. Mace, "Normal Rhythms Associated with Atrioventricular Sequential (DVI) Pacing," Pacing Therapy: A Guide to Cardiac Pacing for Optimum Hemodynamic Benefit, Ch. 13, pp. 191–201 (1983).

P.A. Levine, R.C. Mace, "Assessment and Management of Cross–Talk," Pacing Therapy: A Guide to Cardiac Pacing for Optimum Hemodynamic Benefit, Ch. 13, pp. 239–251 (1983).

P.A. Levine; J.P. Selzer, "Fusion, Pseudofusion, Pseudo–Pseudofusion and Confusion: Normal Rhythms Associated with Atrioventricular Sequential "DVI" Pacing," Clinical Progress in Pacing and Electrophysiology, vol. 1, No. 1, pp. 70–80 (1983).

B.D. Lindsay, S.T. Rothbart, N. Wasty, D. Pantopoulos, S. Saksena, "Prospective Evaluation of Ventricular Pacing and High Energy Transvenous Shocks Using a Triple Electrode Array for Cardioversion of Ventricular Tachycardia," Journal of the American College of Cardiology, vol. 9, No. 2, Supplement A, p. 141A (Feb. 1987).

J.W. Lister, P.P. Tarjan, "The Implantable Electrophysiology Laboratory," Modern Cardiac Pacing, Ch. 43, pp. 759–772 (1985).

A. Lopman, C.L. Langer, S. Furman, D.J.W. Escher, "A Fifteen Year Comparative Study of Cardiac Pacing Costs," The American Journal of Cardiology, vol. 47, p. 392 (Feb. 1981).

B. Lozada, A. Dussaut, H. Mazzetti, M.C. Tenrori, "Chronic Thresholds and Strength–Duration Curve in Chagas Disease," Pace, vol. 8, p. A–110 (May/Jun. 1985, Part II).

R.M. Luceri, A.V. Ramierz, A. Castellanos, L. Zaman, R.J. Thurer, R.J. Myerburg, "Ventricular Tachycardia Produced by a Normally Functioning AV Sequential Demand (DVI) Pacemaker With 'Committed' Ventricular Stimulation," JACC, vol. I, No. 4, pp. 1177–1179 (1983).

B. Maisch, H. Steilner, "Rate Responsive Pacing—Initial Experience with The QT (TX/Quintech) and Biorate Pacemakers," Cardiac Pacemakers (Darmstadt: Steinkopff Verlag) p. 100–106 (1985).

S. Mangiameli, A. Circo, G. Doris, B. Aloisi–Bajunco, M. Abbate, L. Carli, B. Brancati, A. Stuto, N. Digiovanni, G. Bellanca, "Clinical Evaluation Report Topaz: First Dual Sensor Pacemaker," Cardio Stimolazione, vol. 10, No. 3, p. 239 (Sep. 1992).

F.E. Marchlinkski, M. Cain, R.A. Falcone, J.F. Spear, M.E. Josephson, "Changes in Ventricular Refractoriness Following a Premature Stimulus: Implications for Tachycardia Induction," VIIth World Symposium, Pace, vol. 6, No. 3, Part II, p. 509 (May 1983).

A. Markewitz, C. Bernheim, B.M. Kemkes, "Clinical Concerns of the Blanking Period," Pace, vol. 9, p. 293 (Mar./Apr. 1986).

A. Markewitz, K. Wenke, C. Weinhold, "Deterioration of AV Conduction in AAIR Patients: Can it be Predicted Intraoperatively?" PACE, vol. 13, p. 1203 (Sep. 1990).

P. McElroy, K.T. Weber, T.A. Nappholz, "Heart Rate, Ventilation, Mixed Venous Temperature, pH and Oxygen Saturation During Incremental Upright Exercise," Pace, vol. 8, p. 784 (Sep. 1985).

P.A. McElroy, K.T. Weber, J.S. Janicki, T.A. Nappholz, "Mixed Venous Temperature, pH and Oxygen Saturation and Heart Rate During Exercse," Circulation, vol. 72, Suppl. III, p. 1727 (1985).

E.L. Michelson, M. Naito, D. David, E.N. Moore, L.S. Dreifus, "Meobentine Sulfate: Antiarrhythmic Efficacy and Mechanism of Action in a Chronic Canine Model of Myocardial Infarction Suseceptible to Ventricular Tachyarrhythmias," American Journal of Cardiology, vol. 47, p. 392; (Feb. 1981).

D. Morse, "What's Wrong with Pacing?" Pace, vol. 5, pp. 455–456 (May/Jun. 1982).

J. Mugica, M. Mosharrafa, J.P. Letouzey, J.Y. Jacquet, D. MacCarter, M.B. Knudson, "Hemodynamic Demand Pacing: Study of Five Cases," Cardiac Pacing, pp. 1105–1106 (1982).

J. Mugica, S.S. Berold, A. Ripart, "The Smart Pacemaker," New Perspectives in Cardiac Pacing.2, Ch. 23, pp. 545–577 (Sep. 1991).

A.P. Nielsen, J.C. Griffin, W. L. Finke, "Evaluation of Temperature and $O_2$ Saturation during Treadmill Exercise in Older Men: Possible Indices for a Sensor Driven Pacemaker System," JACC, vol. 5, No. 2, p. 393 (1985).

G. Neumann, F. Camerini, "Sick Sinus Syndrome: Long–Term Results With Atrial and Ventricular Pacing," Cardiac Pacing, pp. 989–995 (1982).

R. Norlander, A. Hedman, K. Pehrsson, H. Astrom, "Clinical Experience With Rate Responsive Pacing by the Evoked QT," Pace, vol. 8, p. A–110 (May/Jun. 1985, Part II).

A. Osterspey, H.W. Hopp, V. Hombach, H.J. Deutsch, D.W. Benrenbeck, M. Tauchert, H.H. Hilger, "Diagnostic and Prognostic Significance of Ventricular Late Potentials (VLP) in Patients with Coronary Heart Disease (CHD)," VIIth World Symposium, Pace, vol. 6, No. 3, Part II, p. 561 (May 1983).

G. Palma, F. de Bellis, A. Solinas, M. Falcone, A. Ciccaglioni, A. Venerando, A. Reale, "Sensor–Free Physiological Pacing," Pace, vol. 8, Part II, p. A–21 (May/Jun. 1985).

V.J. Paolone, R. Burian, S. Rosinsky, A.M. Paolone, "Evaluation of the Metabolic Cost of the Three Levels of Exercise Prescribed for Parcourse Stations," Proc. $8^{th}$ Annual Mid–Atlantic Meeting of the American College of Sports Medicine Pennsylvania State University (Feb. 1985).

V. Parsonnet, A.D. Bernstein, "Cardiac Pacing After 25 Years: A Practical Approach to Growing Complexity," Modern Cardiac Pacing, pp. 959–972 (1985).

S.A. Paul, J.M. Tencer, E.L. D'Amico, "Limb Length Evaluation Using the Electrodynogram, a Preliminary Report," Proc. $8^{th}$ Annual Mid–Atlantic Meeting of the American College of Sports Medicine Pennsylvania State University (Feb. 1985).

E.J. Perrins, W.M. Hudson, A. Labiri, E.B. Raftery, "A Randomised Controlled Trial of DDD and Incremental VVI Rate Responsive Pacing," JACC, vol. 3, No. 2, p. 507 (Feb. 1984).

E.V. Platia, "The Electrophysiologic Study," Management of Cardiac Arrhythmias: The Nonpharmacologic Approach, Chap. 5, pp. 62–98 (1987).

T.A. Preston, A.W. Preston, Jr., "The Automatic Rate Adjustment Pacemaker: The Possibilities of Rate Hysteresis," Pace, vol. 1, pp. 178–185 (Apr.–Jun. 1978).

D.R. Ramsdale, R.G. Charles, "Rate–Responsive Ventricular Pacing: Clinical Experience with the RS4–SRT Pacing System," Pace, vol. 8, pp. 378–386 (May/Jun. 1985, Part I).

Special Report of Joint American College of Cardiology/American Heart Association Task Force on Assessment of Cardiac Procedures, "Guidelines for Permanent Cardiac Pacemaker Implantation, May 1984," JACC, vol. 4, No. 2, pp. 434–442 (Aug. 1984).

A.F. Rickards, J. Norman, "Relation Between QT Interval and Heart Rate—New Design of Physiologically Adaptive Cardiac Pacemaker," British Heart Journal, vol. 45, pp. 56–61 (1981).

A.F. Rickards, R.M. Donaldson, "Rate Responsive Pacing," Clin. Prog. Pacing and Electrophysiol., vol. 1, No. 1, pp. 12–19 (1983).

A.F. Rickards, R.M. Donaldson, H.J. Th. Thalen, "The Use of Qt Interval to Determine Pacing Rate: Early Clinical Experience," Pace, vol. 6, pp. 346–354 (Mar./Apr. 1983, Part II).

A.F. Rickards, R.M. Donaldson, "Rate Responsive Pacing Using the TX Pacemaker," VIIth World Symposium, Pace, vol. 6, p. A–12 (May 1983).

A.F. Rickards, "Non Atrial Synchronous Rate Responsive Pacing," Cardiac Pacing, Ch. 17, pp. 755–764 (1985).

A.F. Rickards, "Rate Responsive Pacing," Modern Cardiac Pacing, Ch. 36, pp. 799–809 (1985).

A.F. Rickards, J.F. Godin, "Recommendations for Pulse Generator Clinical Evaluation," European Pacemaker Harmonization Study Group; Stimucoeur, vol. 14, No. 2, pp. 105–111 (1986).

Ph. Ritter, J. Mugica, "Do we Really Need a Fully Automatic Pacemaker?" Eur. J.C.P.E., vol. 2, No. 2, p. A14 (Jun. 1991).

Ph. Ritter, L. Henry, K. Kunisada, S. Cazeau, J. Mugica, "Influence of Programming Settings of Fallback to Ensure 1:1 AV Asscociation During Exercise in Patients with Complete AV Block Paced in DDD Mode with the Chorus II Device," Cardio Stimolazione, vol. 10, No. 3, p. 235 (Sep. 1992).

S. Rogel, Y. Hazin, "Increased Excitability of the Heart Induced by Electrical Stimulation in the Absolute Refractory Period," Chest, vol. 60, No. 6, pp. 578–582 (Dec. 1971).

M. Rosenqvist, H.O. Vallin, K.O. Edhag, "Rate Hysteresis Pacing: How Valuable Is It? A Composition of the Stimulation Rates of 70 and 50 Beats per Minute and Rate Hysteresis in Patients with Sinus Node Disease," Pace, vol. 7, pp. 332–340 (May/Jun. 1984, Part I).

P. Rossi, G. Rognoni, E. Occhetta, M.D. Prando, M. Minella, D.J. McCarter, "Hemodynamic Evaluation of Different Rate Responsive Pacings During Exercise," JACC, vol. 3, No. 2, p. 508 (Feb. 1984).

P. Rossi, G. Rognoni, F. Aina, E. Occhetta, "Permanent Physiological Pacing," G. Ital. Cardiol., vol. 14/II, pp. 784–787 (Oct. 1984).

P. Rossi, F. Aina, G. Rognoni, E. Occhetta, G. Plichi, M.D. Prando, "Increasing Cardiac Rate by Tracking the Respiratory Rate," Pace, vol. 7, pp. 1246–1256 (Nov./Dec. 1984, Part II).

P. Rossi, G. Plicchi, G. Canducci, G. Rognoni, F. Aina, "Respiration as a Reliable Physiological Sensor for Controlling Cardiac Pacing Rate," Br Heart J., vol. 51, pp. 7–14 (1984).

P. Rossi, G. Rognoni, E. Occhetta, F. Aina, M. D. Prando, G. Plicchi, M. Minella, "Respiration–Dependent Ventricular Pacing Compared with Fixed Ventricular and Atrial–Ventricular Synchronous Pacing: Aerobic And Hemodynamic Variables," JACC, vol. 6, No. 3, pp. 646–652 (Sep. 1985).

P. Rossi, "Biosensors: Reliability and Physiologic Specificity," Cardiac Pacing, pp. 765–770 (1985).

Round Table Discussion: "New Techniques for Establishing the Optimal Pacing Rate," Pace, vol. 6, pp. 508–510 (Mar./Apr. 1983, Part II).

Round Table Discussion: "Physiology of Dual–Chamber Pacing," Pace, vol. 6, pp. 355–356 (Mar./Apr. 1983, Part II).

L. Ryden, "Physiological Pacing: Pacemaker Selection," Cardiac Pacing: Electrophysiology and Pacemaker Technology, pp. 1413–1417 (1982).

M. Sami, R. Ripley, "Medtronic Activitrax Pacemaker: Is It Truly Physiologic?" Pace, vol. 8, p. A–78 (May/Jun. 1985, Part II).

R.S. Sanders, U. Brunner, "Use of Pacemaker Diagnostic Data to Optimize DDDR Pacing," Pace, vol. 13, p. 1209 (Sep. 1990).

M. Santini, A. Alliegro, H. Ector, L. Rollies, A. Aubert, G.E. Antonioli, S. Sermasi, J. Mugica, J.P. Letouzey, M. Knudsen, D. Amundson, D.J. MacCarter, "Rate Reponsive Pacing in Man at Various Levels of Activity," Cardiac Pacing, pp. 750–753 (1982).

J.G. Schindler, "Multiple Measurement System for the Electrochemical Analysis of Flowing Liquid and Gases," Biomedizinische Technik, vol. 22, pp. 235–243 (Oct. 1977).

M.H. Schoenfeld, "Innovations of Programmable Functions in Dual Chamber Pacemakers," Eur, J.C.P.E., vol. 4, No. 2, p. 27 (Jun. 1994).

Seip.R. De Meersman, D. Snead, "Reliability Estimate of Exercise Left Ventricular Stroke Volume in Humans Using Impedance Cardiography," Proc. $8^{th}$ Annual Mid–Atlantic Meeting of the American College of Sports Medicine Pennsylvania State University (Feb. 1985).

D. Sellers, J. Knight, N. Fearnot, C. Laubach, W. Johnson, R, Shirey, D. Stevens, "Core Temperature Change with Exercise," Proc. $8^{th}$ Annual Mid–Atlantic Meeting of the American College of Sports Medicine Pennsylvania State University (Feb. 1985).

T.D. Sellers, N.E. Fearnot, W.L. Johnson, R.E. Shirey, D.A. Stevens, D.M. DiLorenzo, J.A. Knight, "Right Ventricular Blood Temperature Profiles for a Physiologic Pacing," Abstracts of the $58^{th}$ Scientific Sessions, p. III–433 (Nov. 1985).

T.D. Sellers, N. Fearnot, W. Johnson, R. Shirey, D. Stevens, "Central Venous Temperature Profiles for a Pacemaker Algorithm," Pace, vol. 8, Part II, p. 294 (Mar./Apr. 1985).

S. Sermasi, M. Marzaloni, M. Marconi, F. Cioppi, and M.A. Mainardi, "1986: Utilization of VVI Rate Responsive Pacing on the Grounds of 754 Consecutive VVI Pacemakers Implanted in 11 Italian Centers," Pace, vol. 13, p. 1210 (Sep. 1990).

J.E. Shapland, D. MacCarter, B. Tockman, M. Knudson, "Physiologic Benefits of Rate Responsiveness," Pace, vol. 6, pp. 329–332 (Mar/.Apr. 1983, Part II).

D.B. Shaw, C.A. Kekwick, A. Whistance, "Bradycardia Detecting Pacemakers: Scope in Diagnosis," VIIth World Symposium, Pace, vol. 6, No. 3, Part II, p. A–153 (May 1983).

B. Shively, N. Goldaschlager, "Progress in Cardiac Pacing," Arch. Intern. Med., vol. 145, pp. 2238–2244 (Dec. 1985).

J. Sholder, P.A. Levine, B.M. Mann, R.C. Mace, "Bidirectional Telemetry and Interrogation in Cardiac Pacing," The Third Decade of Cardiac Pacing, pp. 145–166 (1982).

I. Singer, D. Slater, C. Stavens, J. Kupersmith, "Effects of Ventricular Function on Survival in Patients with Automatic Implantable Cardioverter Defibrillator," Pace, vol. 13, p. 1210 (Sep. 1990).

E. Sowton, "New Frontiers in Clinical Pacing," Cardiac Pacing, pp. 373–374 (1982).

K. Stangl, A. Wirtzfeld, R. Heinze, K. Hoekstein, E. Alt, H.D. Liess, "Oxygen Content and Temperature of Mixed Venous Blood as Physiologic Parameters for Regulating Pacing Rate," Pace, vol. 8, p. A–21 (May/Jun. 1985, Part II).

K. Stangl, A. Wirtzfeld, R. Heinze, K. Hoekstein, E. Alt, H. D. Liess, "Oxygen Content and Temperature of Mixed Venous Blood as Physiological Parameters for Regulating Pacing Rate," Cardiac Pacing, Electrophysiology, Tachyarrhythmias, pp. 810–816 (1985).

K. Stangl, A. Wirtzfeld, O. Lochschmidt, R. Heinze, H. Blomer, Activity–Triggered Pacing: First Clinical Experiences with a New Activity Controlled Pacemaker (Sensulog 703); VIIIth World Symposium, Pace, vol. 10, p. 746 (May–Jun. 1987, Part II).

N. Sulke, A. Dritsas, J. Chambers, E. Sowton, "Is Accurate Rate Response Programming Necessary?" Pace, vol. 13, pp. 1031–1044 (Aug. 1990).

R. Sutton, J. Perrins, P. Citron, "Physiological Cardiac Pacing," PACE, vol. 3, pp. 207–219 (Mar./Apr. 1980).

M.W. Sweesy, R.L. Batey, R.C. Forney, "Crosstalk During Bipolar Pacing," Pace, vol. 11, pp. 1512–1516 (Nov. 1988, Part I).

P.J. van Lake, P.A. Levine, G. A. Mouchawar, "Effect of Implantable Nonthoracotomy Defibrillation System on Permanent Pacemakers: An In Vitro Analysis with Clinical Implications," Pace, vol. 18, pp. 182–187 (Jan. 1995, Park II).

P.J. Vatterott, R.E. Vlietstra, D.L. Hayes, "DDD Pacing: Clinical Considerations," Mayo Clin. Proc., vol. 62, pp. 135–141 (Feb. 1987).

P. Vogt, J.J. Goy, M. Kuhn, P. Leuenberger, L. Kappenberger, "Single Versus Double Chamber Rate Responsive Cardiac Pacing: Comparison by Cardiopulmonary Noninvasive Exercise Testing," Pace, vol. 11, pp. 1896–1901 (Nov. 1988, Part II).

H. von Bibra, U. Busch, K. Stangl, A. Wirzfeld, "The Beneficial Effect of Short AV–Intervals in VDD Pacemaker Patients," Pace, vol. 8, Part II, p. A–69 (May/Jun. 1985,Part II).

B. Waldecker, J. Brachmann, U. Frees, R. Thorspecken, W. Kubler, "Hypersensitivity of the Carotis Sinus—Follow–up after Pacemaker–Implantation," Pace, vol. 9, p. 293 (Mar./Apr. 1986).

M.A. Warnowicz–Papp, "The Pacemaker Patient and the Electromagnetic Environment," Clin. Prog. in Pacing and Electrophysiol., vol. 1, No. 2, pp. 166–176 (1983).

J. Warren, J. Messenger, P. Belott, "A–V Interval Hysteresis: A Provision for Improved Tracking Behavior in a DDD Pacemaker," PACE, vol. 8, p. A–9 (May/Jun. 1985, Part II).

N. Wasty, D. Pantopoulos, S.T. Rothbart, L. Cohen, S. Saksena, "Detection of Sustained Ventricular Tachyarrhythmias Using Right Ventricular Hemodynamic Parameters: A Prospective Study," Journal of the American College of Cardiology, vol. 9, No. 2, Supplement A, p. 141A (Feb. 1987).

S.C. Webb, L.M. Lewis, J. Morris–Thurgood, A. Maseri (Royal Postgraduate Medical School, Hammersmith Hospital, London), "Comparative Assessment of Rate Responsive Pacemakers," Pace, vol. 10, p. 1232 (Sep./Oct. 1987).

M. Wehr, C.G. Schmitt, B. Noll, J. Krappe, P.M. Pittner, B.E. Strauer, "The Effect of Heart Rate and AV Interval on Left Ventricular Ejection Time (LVET) and Contractility (PEP/LVET) in Patients with AV Universal Pacemakers," Pace, vol. 8, p. A–9 (May/Jun. 1985, Part II).

B.J. Whipp, J.A. Davis, F. Torres, K. Wasserman (Division of Respiratory Physiology and Medicine, Harbor–UCLA Medical Center, Torrance, California), "A Test to Determine Parameters of Aerobic Function During Exercise," Journal of Applied Physiology, vol. 50, pp. 217–221 (1981).

J.R. Windle, W.M. Miles, D.P. Zipes, E.N. Prystowsky, "Prolongation of Human Ventricular Refractoriness by Sub-threshold Stimuli: Effect of Heart Rate, Pulse Width and Current Strength," Circulation, Part II, vol. 70, No. 4, p. II–201 (Oct. 1984).

A. Wirtzfeld, L. Goedel–Meinen, T. Bock, R. Heinze, H.D. Liss, J. Muntaenu, "Central Venous Oxygen Saturation for the Control of Automatic Rate–Reponsive Pacing," Pace, vol. 5, pp. 829–835 (Nov./Dec. 1982).

A. Wirtzfeld, K. Stangl, R. Heinze, Th. Bock, H. D. Liess, E. Alt, "Mixed Venous Oxygen Saturation for Rate Control of an Implantable Pacing System," Cardiac Pacing, pp. 271–279 (1983).

A. Wirtzfeld, K. Stangl, R. Heinze, T. Bock, E. Alt, "An Active Optical Sensor for Monitoring Mixed Venous Oxygen Saturation for an Implantable Rate–Responsive Pacing System," Pace, vol. 6, p. A–12 (May 1983).

A. Wirtzfeld, R. Heinze, K. Stanzl, K. Hoekstein, E. Alt, H. D. Liess, "Regulation of Pacing Rate by Variations of Mixed Venous Oxygen Saturation," Pace, vol. 7, pp. 1257–1262 (Nov./Dec. 1984, Part II).

A. Wirtzfeld, K. Stangl, G. Schmidt, "Physiological Pacing: AV–Synchrony and Rate Control," Modern Cardiac Pacing, pp. 875–892 (1985).

Y. Yamamoto, J. Sugai, "Atrial Contribution in VVI Pacing," Pace, vol. 6, No. 3, Part II, p. A0153 (May 1983).

F.I. Zacouto, L.J. Guize, "Fundamentals of Orthorhythmic Pacing," Cardiac Pacing: Diagnostic and Therapeutic Tools, pp. 213–218 (1976).

M. Zegelman, F. Beyersdorf, J. Kreuzer, N. Reifart, J. Happ, "Adaptation of Heart Rate to Exercise. Comparison of QT–Related and Respiratory Dependent Pacemakers," Progress In Clinical Pacing, pp. 104–110 (1984).

M. Zegelman, N. Treese, P. Sammer, J. Kreuzer, S. Classen, E. Lichter, A. Wemeyer, "The Belief in VVIR—An Illusion," Cardio Stimolazione, vol. 10, No. 3, p. 233 (Sep. 1992).

D.P. Zipes, E.N. Prystowsky, W.M. Miles, J.J. Heger, "Initial Experience with Symbios Model 7008 Pacemaker," Pace, vol. 17, pp. 1301–1305 (Nov./Dec. 1984, Part II).

F.T. Zugibe, N.C. Nanda, T. Akiyama, S.S. Barold, "Doppler Detection and Quantitation of Mitral Regurgitation During Ventricular and Atrioventricular Sequential Pacing," JACC, vol. 3, No. 2, p. 508 (Feb. 1984).

Intermedics Cardiac Pulse Generator Physician's Manual: Cosmos (Models 283–01V and 284–02V), Intermedics, Inc. (Jun. 1988).

Delta TRS (Models 937/938 Type DDD, Dual–Chamber Pulse Generators): Physician's Manual, Cardiac Pacemakers, Inc. (Oct. 1988).

Delta T and Delta TRS (Model 2025 Software Module) Operator's Manual, Cardiac Pacemakers, Inc. (1988).

Intermedics Cardiac Pulse Generator Physician's Manual: Cosmos II (Models 283–03 and 284–05), Intermedics, Inc. (Dec. 1993).

Diamond Multisensor Dual Chamber Pacemaker: Reference Guide, Vitatron Medical B.V. (1993).

Intermedics Physician's Manual: Cosmos 3 Cardiac Pulse Generators, Intermedics, Inc. (Apr. 1996).

Fearnot, N.E. et al., *"A Review of Pacemakers That Physiologically Increase Rate: The DDD and Rate–Responsive Pacemakers,"* Progress in Cardiovascular Diseases, vol. XXIV, No. 2 Sep./Oct. 1986: pp. 145–164.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–9, 11, 12 and 14–18 are cancelled.

Claims 10, 13, 19 and 20 are determined to be patentable as amended.

New claims 21, 22, 23, 24 and 25 are added and determined to be patentable.

[1. An improved dual chamber pacemaker having programmable modes of operation, said pacemaker being capable of stimulating the atrial and the ventricular chambers of the heart, said pacemaker including programming means for selectively allowing the pacemaker to be programmed to operate in an atrial rate based mode of operation, and atrial sensing means for sensing atrial activity occurring in the atrial chamber, including atrial rate of said atrial activity, wherein the improvement comprises:

first sensing means for monitoring said atrial rate and sensing whether said atrial rate exceeds a first prescribed threshold;

means for providing a stimulating pulse to a selected chamber of the heart at a maximum upper rate in the event said atrial rate sensed by said first sensing means exceeds said first prescribed threshold;

second sensing means for monitoring said atrial rate above said first prescribed threshold and sensing whether said atrial rate exceeds a second prescribed threshold, said second threshold being at a higher rate than said first threshold; and means for automatically switching the mode of operation of said pacemaker from said atrial rate based mode of operation to a selected alternate mode of operation in the event said atrial rate exceeds said second prescribed threshold.]

10. [The] *An improved dual chamber* pacemaker [of claim 9] *having programmable modes of operation, said pacemaker being capable of stimulating the atrial and the ventricular chambers of the heart, said pacemaker including programming means for selectively allowing the pacemaker to be programmed to operate in an atrial rate based mode of operation, and atrial sensing means for sensing atrial activity occurring in the atrial chamber, including atrial rate of said atrial activity, wherein the improvement comprises:*

*first sensing means for monitoring said atrial rate and sensing whether said atrial rate exceeds a first prescribed threshold;*

*means for providing a stimulating pulse to a selected chamber of the heart at a maximum upper rate in the event said atrial rate sensed by said first sensing means exceeds said first prescribed threshold;*

*second sensing means for monitoring said atrial rate above said first prescribed threshold and sensing whether said atrial rate exceeds a second prescribed threshold, said second threshold being at a higher rate than said first threshold; and*

*means for automatically switching the mode of operation of said pacemaker from said atrial rate based mode of operation to a selected alternate mode of operation in the event said atrial rate exceeds said second prescribed threshold;* the pacemaker further comprising atrial sensitivity adjustment means for automatically checking the sensitivity of said atrial sensing means at selected intervals to determine its ability to sense P-waves, and for automatically adjusting said atrial sensing means to sense P-waves in the event that P-waves are not being sensed, wherein said atrial sensitivity adjustment means comprises:

means for switching said pacemaker to a test mode of operation;

means for monitoring said atrial sensing means during said test mode for a prescribed period of time to determine if any P-waves are detected; and means for adjusting said atrial sensing means so that lower amplitude P-waves can be detected by said atrial sensing means in the event no P-waves are detected by said monitoring means during said prescribed period of time;

*wherein said means for adjusting said atrial sensing means comprises means for adjusting the sensitivity of said atrial sensing means in a series of incremental adjustments until said P-waves are detected; and*

*wherein said pacemaker further comprises:*

*means for switching the pacemaker mode of operation from said test mode to a prescribed alternate mode of operation in the event P-waves are not detected after the sensitivity of said atrial sensing means has been adjusted through all of said fixed incremental adjustments, whereby said alternate mode of operation provides an indicia that said atrial sensing means was unable to detect P-waves.*

13. [The] *A dual chamber* pacemaker [of claim 11 further] *having first and second channels, said first and second channels including sensing means for sensing cardiac activity and pulse generating means for providing pacing pulses in the absence of cardiac activity in the atrial and the ventricular chambers of the heart, respectively, said pacemaker comprising:*

*control means for controlling said sensing means and said pulse generating means of said first and second channels in a prescribed mode of operation, said control means comprising:*

*means for detecting a rate of cardiac activity as sensed by said sensing means in said first channel; and*

*means for triggering said pulse generating means to provide pacing pulses in said second channel at a rate which is the lesser of said rate of cardiac activity detected in said first channel or a maximum tracking rate; and*

*means for automatically changing said prescribed mode of operation in the event said rate of cardiac activity detected in said first channel exceeds a specified threshold level, said specified threshold level comprising a rate which is greater than said maximum tracking rate;* the pacemaker further comprising:

means for automatically adjusting the ability of said first channel to sense cardiac activity, *comprising means for* adjusting the sensitivity of the sensing means in the first channel in a series of incremental adjustments until cardiac activity is detected in the first channel; and means for switching the mode of operation of said pacemaker from said prescribed mode of operation to a prescribed alternate mode of operation in the event cardiac activity is not detected in said first channel after the sensitivity of the sensing means in the first channel has been adjusted through said series of incremental adjustments.

19. [The] *A* method of [claim 18] *operating a dual chamber programmable pacemaker, said pacemaker being capable of operating in a variety of modes of operation and being initially programmed to operate in an atrial rate based mode of operation, said pacemaker comprising means for sensing cardiac activity in the atrial and the ventricular chambers of a heart, and means for selectively providing a stimulating pulse to either chamber of the heart at prescribed times and under prescribed conditions, the method comprising the steps of:*

(a) *sensing when the atrial rate exceeds a first rate threshold;*

(b) *providing a stimulating pulse to a selected chamber of the heart at a maximum upper rate in the event the atrial rate sensed in step (a) exceeds said first rate threshold;*

(c) *monitoring the atrial rate above said first rate threshold up to a second rate threshold; and*

(d) *automatically switching the mode of operation of said pacemaker from said atrial rate based mode of operation to a selected alternate mode of operation in the event the atrial rate exceeds said second rate threshold;*

*the method further comprising the step of:*

(e) *checking the sensitivity of the atrial sensing means at selected intervals to determine its ability to sense P-waves; and*

(f) *automatically adjusting the sensitivity of the atrial sensing means to sense P-waves in the event that P-waves are not being sensed;* wherein the step of checking the sensitivity of the atrial sensing means comprises:

monitoring the atrial sensing means for a specified period of time to determine if any P-waves are detected, *and* switching the pacemaker mode of operation from said atrial rate based mode of operation to a prescribed alternate mode of operation in the event P-waves are not detected during said prescribed period of time.

20. [The] *A* method of [claim 18] *operating a dual chamber programmable pacemaker, said pacemaker being capable of operating in a variety of modes of operation and being initially programmed to operate in an atrial rate based mode of operation, said pacemaker comprising means for sensing cardiac activity in the atrial and the ventricular chambers of a heart, and means for selectively providing a stimulating pulse to either chamber of the heart at prescribed times and under prescribed conditions, the method comprising the steps of:*

(a) *sensing when the atrial rate exceeds a first rate threshold;*

(b) *providing a stimulating pulse to a selected chamber of the heart at a maximum upper rate in the event the atrial rate sensed in step (a) exceeds said first rate threshold;*

(c) *monitoring the atrial rate above said first rate threshold up to a second rate threshold; and*

(d) *automatically switching the mode of operation of said pacemaker from said atrial rate based mode of operation to a selected alternate mode of operation in the event the atrial rate exceeds said second rate threshold;*

*the method further comprising the step of:*

(e) *checking the sensitivity of the atrial sensing means at selected intervals to determine its ability to sense P-waves; and*

(f) *automatically adjusting the sensitivity of the atrial sensing means to sense P-waves in the event that P-waves are not being sensed;* wherein the step of adjusting the sensitivity to sense P-waves comprises:

changing the sensitivity of the atrial sensing means by a first discrete increment;

checking the sensitivity of the atrial sensing means to determine if P-waves are sensed;

if P-waves are not sensed, changing the sensitivity of the atrial sensing means again by a second discrete increment, checking the sensitivity of the atrial sensing means again to determine if P-waves are sensed, and so on, through a series of discrete increments, until P-waves are sensed; *and*

*if P-waves are not sensed after said series of discrete increments, switching the pacemaker mode of operation from said atrial rate based mode of operation to a prescribed alternate mode of operation.*

*21. The programmable pacemaker of claim 10, wherein said first sensing means and said second sensing means each comprise logic implemented using a combination of (a) hardware and (b) software or firmware.*

*22. The programmable pacemaker of claim 10, wherein said second sensing means comprises logic for sensing whether said atrial rate exceeds said second prescribed threshold based on monitoring a plurality of P-wave cycles.*

*23. The programmable pacemaker of claim 10, wherein said means for providing a stimulation pulse at a maximum upper rate comprises hardware, software and/or firmware to ensure that a stimulation pulse is not delivered to said selected chamber of the heart at a rate that exceeds a maximum upper limit.*

*24. The method of any of the claims 19 or 20, wherein sensing step (a) comprises sensing when the atrial rate exceeds a first rate threshold based on monitoring a plurality of P-wave cycles.*

*25. The method of any of the claims 19 or 20, wherein step (b) of providing a stimulating pulse at a maximum upper rate comprises ensuring that stimulating pulses are not provided to said selected chamber of the heart at a rate that exceeds a maximum upper limit.*

* * * * *